United States Patent [19]

Bartels-Keith et al.

[11] 4,442,290
[45] Apr. 10, 1984

[54] DEVELOPMENT RESTRAINER RELEASE COMPOUNDS

[75] Inventors: James R. Bartels-Keith, Lexington; Anthony J. Puttick, Arlington, both of Mass.

[73] Assignee: Polaroid Corporation, Cambridge, Mass.

[21] Appl. No.: 362,651

[22] Filed: Mar. 29, 1982

Related U.S. Application Data

[62] Division of Ser. No. 273,039, Jun. 12, 1981, Pat. No. 4,350,754.

[51] Int. Cl.³ .................. C07D 403/06; C07D 403/12
[52] U.S. Cl. .................................... 544/310; 548/251; 544/276; 544/296
[58] Field of Search ..................... 544/310, 276, 296

[56] References Cited

U.S. PATENT DOCUMENTS 4,350,752 9/1982 Reczek et al. ............... 430/219
4,355,092 10/1982 Mehta et al. ................ 430/219
4,355,101 10/1982 Mehta et al. ................ 430/219

OTHER PUBLICATIONS

Guglielmi, Hoppe–Seyler's Z. Physiol. Chem., 349(12), pp. 1733–1738 (1968).

*Primary Examiner*—Paul M. Coughlan, Jr.
*Attorney, Agent, or Firm*—Gaetano D. Maccarone

[57] ABSTRACT

There are described novel compounds which are represented by the formula

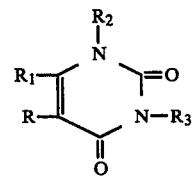

wherein R is

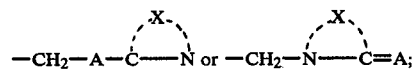

A is sulfur or selenium; X represents the nonmetallic atoms necessary to form a nucleus which completes a five or six membered heterocyclic moiety; $R_1$ is H or lower alkyl; $R_2$ is H or a hydrolyzable group; and $R_3$ is H, alkyl or a hydrolyzable group. The compounds are useful in photographic applications and provide controlled release of a photographically useful material during processing of photographic elements with an aqueous alkaline processing composition.

18 Claims, No Drawings

DEVELOPMENT RESTRAINER RELEASE COMPOUNDS

CROSS-REFERENCE TO RELATED APPLICATIONS

This application is a division of prior copending application Ser. No. 273,039, filed June 12, 1981 now U.S. Pat. No. 4,350,754.

BACKGROUND OF THE INVENTION

It is known in the art to utilize development restrainers and development restrainer precursors in photographic applications. A predetermined level of development usually will take place before the development restrainers or development restrainer precursors function to inhibit or control further development. The blocked development restrainers are designed to provide a timed release of the development restrainer during the development process. Such blocked development restrainers are disclosed, for example, in U.S. Pat. Nos. 3,260,597 and 3,265,498 which disclose hydrolyzable blocked restrainers; U.S. Pat. No. 3,698,898 which discloses the use of quinone- or naphthoquinonemethide precursors which release a photographic reagent such as 1-phenyl-5-mercaptotetrazole in the presence of alkali; U.S. Pat. No. 4,009,029 which discloses a class of cyanoethyl-containing blocked development restrainers; and German Offenlegungsschrift No. 2,427,813 which discloses various blocked development restrainers.

The present application relates to novel compounds which are useful in photographic applications as well as photographic products and processes which utilize the compounds.

SUMMARY OF THE INVENTION

It is therefore an object of this invention to provide novel compounds.

Another object is to provide compounds which are useful in photographic applications.

It is another object to provide compounds which are useful in photographic applications as blocked development restrainers.

A further object is to provide compounds which allow controlled release of a photographically useful material during processing of a photographic element.

Still another object is to provide photographic products and processes utilizing the compounds.

BRIEF SUMMARY OF THE INVENTION

These and other objects and advantages are accomplished in accordance with the invention by providing novel compounds which are represented by the formula

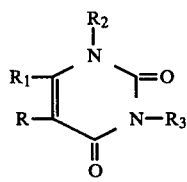

FORMULA A wherein R is

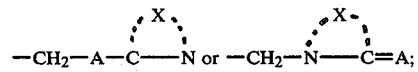

A is sulfur or selenium; X represents the nonmetallic atoms necessary to form a five or six-membered heterocyclic moiety including substituted rings and fused rings; $R_1$ is H or lower alkyl having from 1 to 6 carbon atoms; $R_2$ is H or a hydrolyzable group such as an acyl group such as, for example, acetyl or benzoyl or an ester group such as, for example,

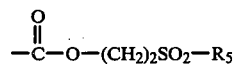

where $R_5$ may be alkyl, preferably having from 1 to 6 carbon atoms or aryl such as phenyl, or

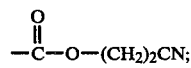

and $R_3$ is H, alkyl or a hydrolyzable group such as those described above.

It should be noted that when $R_2$ and $R_3$ are hydrogen the tautomeric form of the compounds represented by Formula A also may be represented as follows:

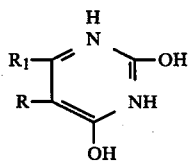

FORMULA B

It should be understood that both tautomeric forms of the compounds are intended to be encompassed by Formula A.

The novel compounds are generally azoles which cleave in alkaline compositions to provide mercaptoazoles which are diffusible in aqueous alkaline photographic processing compositions. As stated previously, the heterocyclic moiety includes substituted rings and fused rings. Where the heterocyclic moiety is substituted the substituent(s) may be attached to either a nitrogen atom or a carbon atom of the azole moiety. The preferred heterocyclic rings within generic Formula A include groups wherein the heterocyclic atoms, i.e., atoms other than carbon, are members of a single heterocyclic ring rather than fused or condensed heterocyclic rings wherein the heterocyclic atoms are members of more than one heterocyclic ring. The compounds of the invention include monoazoles such as benzoxazoles, benzothiazoles, etc.; imidazoles; triazoles such as 1,2,4-triazoles, benzotriazoles, etc.; tetrazoles and pyrimidines. The most preferred heterocyclic rings are tetrazoles and a particularly preferred ring is a phenyl substituted tetrazole which may also be substituted on the phenyl ring.

The blocking moiety of the compounds provides a timed release of a photographically useful material in the alkaline environment typically encountered in the processing of photographic elements and particularly where the alkaline medium has a relatively high pH, e.g. in the range of from about 12 to about 14. The rate of release of the photographically useful material is dependent upon the hydroxyl ion concentration and therefore the rate of release increases as the pH increases. Upon cleavage of the molecule the heterocyclic ring taken together with the sulfur atom provides a photographically useful material. The cleavage reaction occurs according to the following sequence, for example,

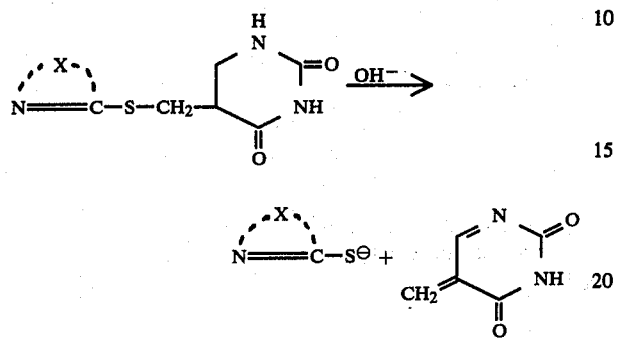

The rate of release of the azole moiety is also temperature dependent, that is, it is released at a rate which increases with the temperature at which processing of the film unit is effected. Thus, more of the azole moiety is made available at elevated temperatures, i.e., above room temperature, where more is typically desired, less is released at room temperature and even less below room temperature where lesser amounts are needed. Thus, these blocked compounds which are utilized according to the invention provide more uniform sensitometry for the film units of the invention over a wide temperature range of processing. In other words, the sensitometry of the film units which include such blocked compounds according to the invention is less temperature dependent than would otherwise be the case.

In one preferred embodiment such as, for example, where the azole moiety is a phenyl substituted tetrazole, the compounds of the invention are useful in photographic applications as blocked development restrainers. When incorporated into a photographic element these compounds permit initial development to occur normally during processing of the element with an aqueous alkaline processing composition and then undergo cleavage to restrain or control further development. Upon cleavage of the molecule the heterocyclic ring taken together with the sulfur atom provides a silver halide development restrainer. As mentioned above, the blocking moiety provides timed release, i.e., release after a predetermined time, of the development restrainer moiety in the alkaline environment encountered during photographic processing. When the azole moiety is substituted with a phenyl ring the latter may be attached to a nitrogen atom or a carbon atom.

A preferred group of compounds according to the invention are those wherein the azole moiety is represented by either of the formulas

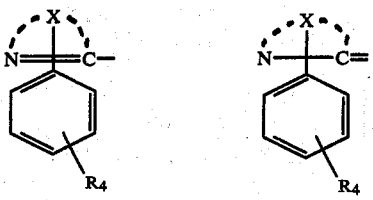

FORMULA C          FORMULA D wherein $R_4$ is either a group which has a pKa of from about 7 to about 14, preferably at least about 8.5 or higher, which is ionizable to an anion whereby the silver salt of the moiety resulting from cleavage of the blocking group is more soluble in the pH range within which $R_4$ is ionized to an anion than it is below that pH range, or a precursor of such a group. Typical substituents which are useful as $R_4$ include:

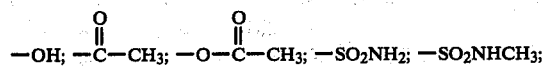

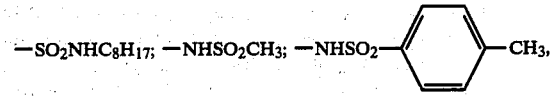

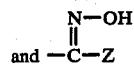

where Z is H, alkyl having from 1 to 10 carbon atoms, aralkyl such as benzyl or phenethyl, phenyl or substituted phenyl. Upon cleavage of the molecule as described above there is provided a photographically useful material which provides desirable results such as will be described in detail below herein.

As stated above, $R_4$ may also be a precursor of a substituent which has the requisite properties and the desired substituent may be formed in situ. For example, it is possible to incorporate in the film unit as a precursor a compound having an azole moiety within Formulas C or D which has a hydrolyzable ester group on the phenyl ring and generate the desired hydroxy group in situ during photographic processing. It should be noted here that the acetyl group which can be substituted on the phenyl ring does not ionize to any appreciable extent to form an anion in an aqueous alkaline processing composition. However, the presence in a film unit of a compound having an azole moiety within Formula C or D having an acetyl group substituted on the phenyl ring can provide advantageous results. It would appear that the compound undergoes a change in aqueous alkaline processing composition and that the acetyl substituent is a precursor of a group which has the requisite properties described above which provide the desired results.

As disclosed previously, $R_2$ may be H or a hydrolyzable group. Any suitable hydrolyzable group may be attached to the nitrogen atom in that position such as, for example, an acyl group such as acetyl or benzoyl; an ester group such as, for example,

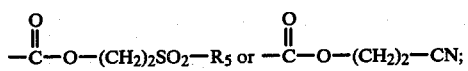

or —CH$_2$—CH$_2$—Y where Y is cyano

or —SO$_2$R$_5$ and R$_5$ is as previously defined. The presence of a hydrolyzable group in this position will prevent any release of the photographically useful moiety. Release of the photographically useful moiety will occur only when the group is hydrolyzed upon contact with an aqueous alkaline medium. The substituent R$_3$ may be H, alkyl or a hydrolyzable group. The hydrolyzable group may be any suitable group such as, for example, those described above.

DESCRIPTION OF THE PREFERRED EMBODIMENTS

Preferred compounds according to the invention include those which are represented by the formulas

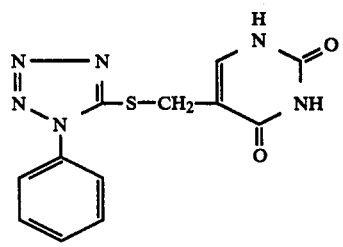
(I)

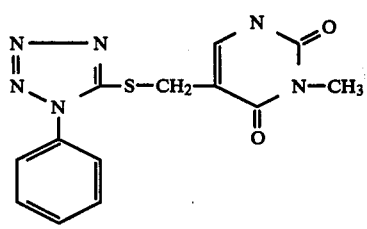
(II)

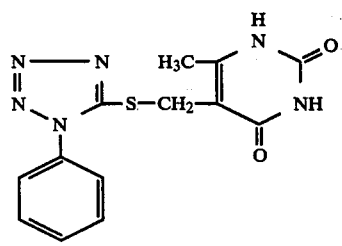
(III)

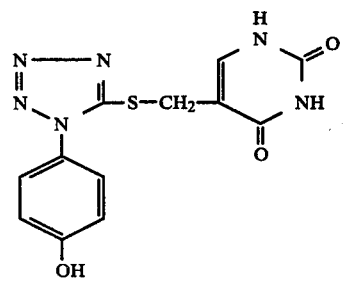
(IV)

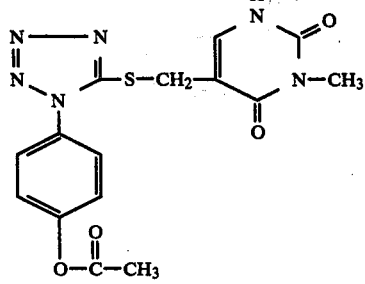
(V)

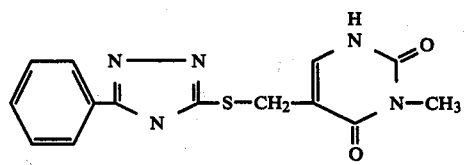
(VI)

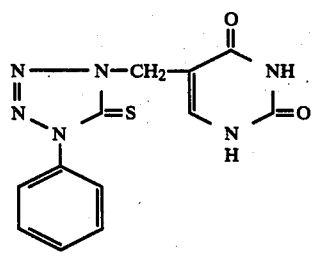
(VII)

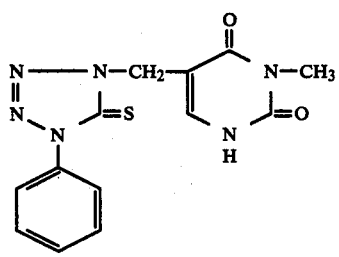
(VIII)

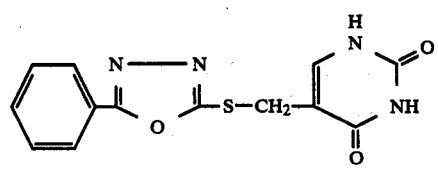
(IX)

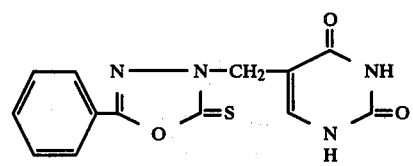
(X)

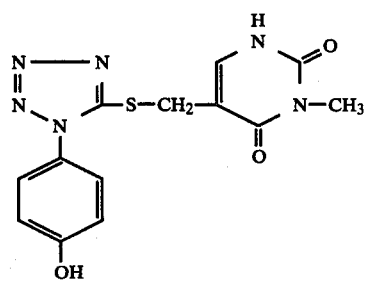
(XI)

-continued
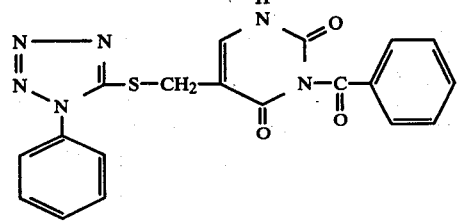 (XII)
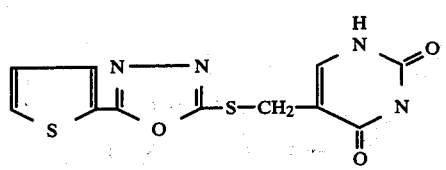 (XIII)
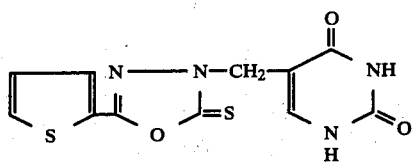 (XIV)
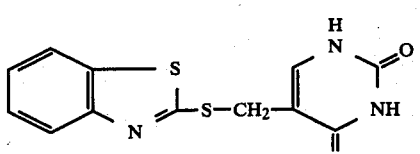 (XV)
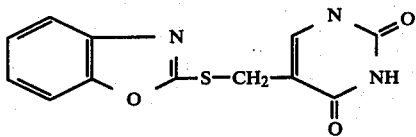 (XVI)
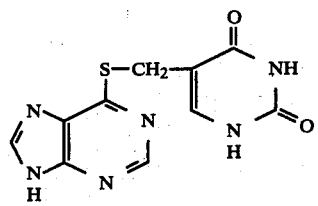 (XVII)
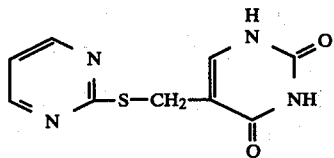 (XVIII)
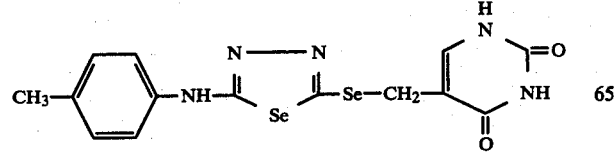 (XIX)
-continued
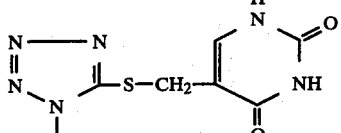 (XX)
 (XXI)
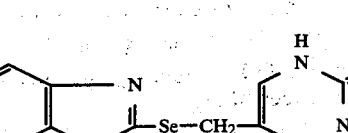 (XXII)
 (XXIII)
 (XXIV)
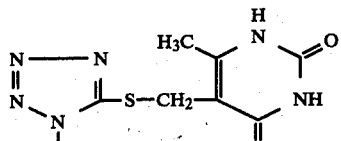 (XXV)

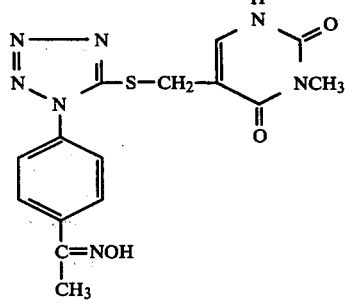 (XXVI)

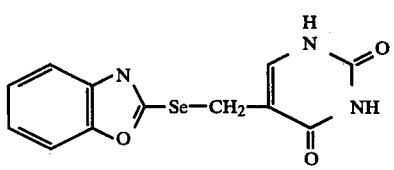 (XXVII)

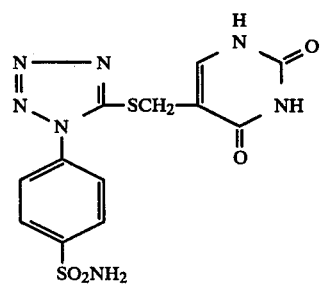 (XXVIII)

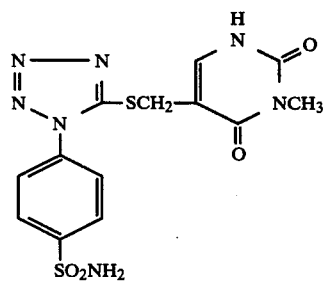 (XXIX)

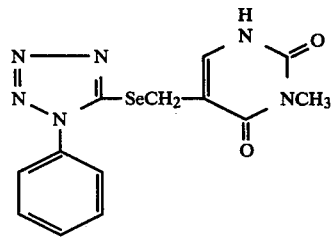 (XXX)

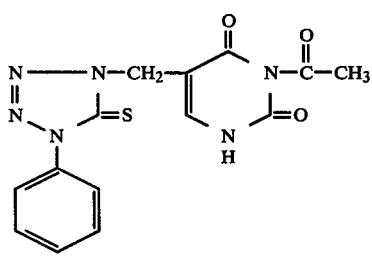 (XXXI)

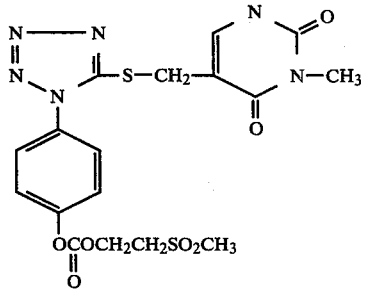 (XXXII)

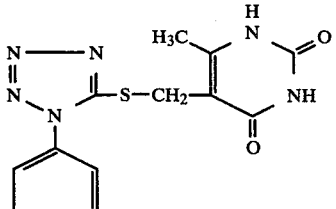 (XXXIII)

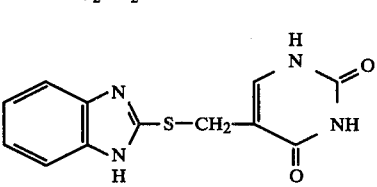 (XXXIV)

Generally, the compounds of the invention may be prepared by reacting the appropriate photographically useful moiety with a suitable base such as sodium methoxide in a solvent such as methanol or dimethylformamide to form a salt and subsequently reacting the salt with chloromethyl uracil or the appropriate substituted chloromethyluracil in a solvent such as dimethylformamide at a temperature in the range of from about −10° C. to room temperature. The starting materials are commercially available in some cases and generally can be made by reactions which are known to those of ordinary skill in the art. For example, 2-mercaptoimidazoles can be prepared by the reactions disclosed in the Chemistry of Heterocyclic Compounds Vol. 6: Imidazole and Its Derivatives, Part I, Hoffman, Interscience Publishers, Inc., New York, 1953, pages 77–85; mercaptothiazoles and mercaptobenzothiazoles can be prepared according to the methods disclosed in The Chemistry of Heterocyclic Compounds Vol. 34: Thiazole and Its Derivatives, Part I, Metzger, John Wiley and Sons, 1979, pages 260–269; Part 2, pages 370–377; benzoxazolethiazones can be prepared according to the methods disclosed in Heterocyclic Compounds, Vol. 5, Elderfield, John Wiley and Sons, 1957, pages 439–444; 5-mercapto-1,3,4-oxadiazoles can be prepared according to the methods disclosed in Heterocyclic Compounds, Vol. 7, Elderfield, John Wiley and Sons, 1961, page 352; mercapto-1,3,4-thiadiazoles, ibid, pages 587–612; and tetrazoles by the techniques disclosed in Heterocyclic Compounds, Vol. 8, Elderfield, John Wiley and Sons, 1967, pages 1–107. Mercapto-1,2,4-triazoles can be prepared by known literature techniques as described, for example, in Jour. Chem. Soc. E. Hoggarth 1163 (1949). The selenazoles may be prepared by similar techniques.

Copending patent application Ser. No. 222,543, filed Jan. 5, 1981, now U.S. Pat. No. 4,355,092, discloses novel phenylmercaptoazole compounds which include an oxime substituent on the phenyl ring and discloses techniques for their preparation.

As discussed previously, the rate of release of the photographically useful moiety from the compounds is dependent upon the hydroxyl ion concentration of the aqueous alkaline environment and temperature. In addition, the compounds release the photographically useful moiety at varying rates dependent upon where the blocking group is connected to the azole moiety, that is, whether the blocking group is attached to a sulfur atom or a nitrogen atom, and also upon electrostatic effects brought about by the ionization of atoms in the molecule upon contact with an aqueous alkaline medium which could reduce the rate at which the release mechanism occurs. These variables permit the selection of a compound having release rates desired for a particular application.

The release kinetics in solution of the compounds of the invention vary over a wide range. The $t_{\frac{1}{2}}$ times in solution, i.e., the time required for one half of the molecule to undergo cleavage and release the azole moiety, for some of the compounds illustrated above are shown in Table I. These data were obtained using $1 \times 10^{-4}$ molar concentrations in 30% acetonitrile/0.25 N aqueous potassium hydroxide solution at a temperature of $22° \pm 0.1°$ C., unless otherwise noted.

TABLE I

| COMPOUND | $t_{\frac{1}{2}}$ (sec) | COMPOUND | $t_{\frac{1}{2}}$ (sec) |
|---|---|---|---|
| I | 0.0033 | XVII | 77.8 |
| II | 0.81 | XVIII | 35.9 |
| III | 0.0011 | XIX | 48.8** |
| IV | 0.011 | XX | { 0.0024 <br> 2.5 (hydrolysis) |
| V | 1.8–4.0* | | |
| VI | 0.16 | XXI | 0.004 |
| VII | 900 | XXII | 0.005*** |
| VIII | 1512 | XXIII | 0.0039 |
| IX | 0.0017 | XXIV | 0.011 |
| X | 1080 | XXV | 0.0049 |
| XI | 4.0 | XXVI | 0.87 |
| XII | 31.2 | XXVII | 0.00074 |
| XIII | 0.0011 | XXVIII | 0.004 |
| XIV | 4320 | XXIX | 0.4 |
| XV | 0.068 | XXX | 0.15 |
| XVI | 0.011 | XXXI | { 0.16 (hydrolysis) <br> 911 |

*rate of hydrolysis approximates rate of release
**measured in 50% ethanol/water solution
***solution was 0.022N in KOH The compounds of the invention may be present in photographic elements in any appropriate location and in any amount which is required to accomplish their intended purpose. The amount necessary in any particular instance is dependent upon a number of factors such as, for example, the compound utilized, the type of photographic element, the location of the compound in the photographic element and the result desired. Routine scoping tests may be used to ascertain the concentration appropriate for any given photographic element. In a preferred embodiment of the invention the compounds are incorporated in diffusion transfer photographic film units as will be discussed in more detail below herein. In such film units the compounds may be incorporated in the photosensitive element and/or the image-receiving element or in a cover sheet.

The novel compounds of the invention may be utilized in any photographic system wherein the release of a development restrainer is desired during processing. Further, the compounds can be utilized in various layers of a multilayer photographic system in varying concentrations to ensure the desired distribution of the development restrainer during processing.

As disclosed previously, the compounds of the invention are particularly useful in diffusion transfer photographic systems. Generally such compounds can provide desirable results when the diffusion transfer photographic processing is carried out at room temperature and particularly where the processing is carried out at elevated temperature, e.g., about 95° F. These desirable results include the control of fog development as a function of the processing temperature, that is, control of fog development due to elevated temperatures while not adversely affecting processing at lower temperatures. As pointed out above, these blocked compounds provide more uniform sensitometry over a wide temperature range of processing.

The advantageous results which can be obtained through the use of a preferred species of the compounds according to the invention, that is, those which include a substituted phenyl moiety as illustrated in Formulas C and D, are not completely understood. However, to further aid those skilled in the art to understand and practice the invention, the proposed theoretical mechanism by which the advantageous results are thought to be effected will be discussed here. It should be understood, however, that the diffusion transfer photographic system has been proved to be operative and highly effective through extensive experimentation and the proposed theoretical mechanism is not to be construed as being limiting of the invention.

It is theorized that such results are obtainable because the compounds which are released as a result of the cleavage of the blocking moiety during processing perform different functions at different stages of the development process, that is, as weak silver solvents and promoters of development at one stage of the development process and as development restrainers, or inhibitors, at another stage of the process, and that the dual functions of these compounds within the diffusion transfer photographic system are pH dependent.

It is well known that in the diffusion transfer development process the pH of any particular location within the film unit varies with time. Typically, the processing composition employed in the process has a very high pH, e.g., from about 13–14 and during the development process each layer of the multilayer film unit goes through a broad pH range which includes very high pH levels and relatively low pH levels. When the pH is substantially equal to or above the pKa of the substituent $R_4$ on the phenyl ring, the dianion is formed, for example,

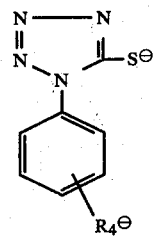

and acts as a weak silver solvent to form relatively soluble silver salts, thus promoting development. When the pH falls below the pKa of the substituent $R_4$, the monoanion is formed, for example,

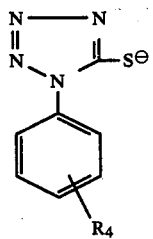

and the silver salt of the monoanion of the compound is very low in solubility resulting in a development restrainer action.

In view of the foregoing, it will be understood that when it is desired to utilize both functions, development of the exposed photosensitive element in the presence of such compounds is carried out with a processing composition having a pH substantially equal to or above the pKa of the particular substituent, at least for some period of time, when the processing composition comes into contact with the compound so as to enable the blocking moiety to cleave and the substituent($R_4$) to ionize to form the dianion. In addition, at some point during the development process, the pH of the environment where the compound is located will go below the pKa of the substituent so as to enable the monoanion to be formed again. Of course, if it is desired to utilize only the development restrainer effect a processing composition having a pH lower than the pKa of the substituent could be used.

The novel compounds of the invention may be used in conjunction with any photographic emulsion. It is preferred to use these compounds in a diffusion transfer photographic system, particularly one which includes a negtive working silver halide emulsion, i.e., one which develops in the areas of exposure. Further, these compounds may be used in association with any image dye-providing materials. In a particularly preferred embodiment the diffusion transfer phtographic film elements of the invention include one or more image dye-providing materials which may be initially diffusible or nondiffusible. In diffusion transfer photographic systems the image dye-providing materials which can be utilized generally may be characterized as either (1) initially soluble or diffusible in the processing composition but which are selectively rendered nondiffusible imagewise as a function of development; or (2) initially insoluble or nondiffusible in the processing composition but which selectively provide a diffusible product imagewise as a function of development. The image dye-providing materials may be complete dyes or dye intermediates, e.g., color couplers. The requisite differe5tial in mobility or solubility may be obtained, for example, by a chemical reaction such as a redox reaction, a coupling reaction or a cleavage reaction. In a particularly preferred embodiment of the invention the image dye-providing materials are dye developers which are initially diffusible materials. The dye developers contain, in the same molecule, both the chromophoric system of a dye and a silver halide developing function as is described in U.S. Pat. No. 2,983,606. Other image dye-providing materials which may be used include, for example, initially diffusible coupling dyes such as are useful in the diffusion transfer process described in U.S. Pat. No. 3,087,817 which are rendered nondiffusible by coupling with the oxidation product of a color developer; initially non-diffusible dyes which release a diffusible dye following oxidation, sometimes referred to as "redox dye releaser" dyes, described in U.S. Pat. Nos. 3,725,062 and 4,076,529; initially nondiffusible image dye-providing materials which release a diffusible dye following oxidation and intramolecular ring closure as are described in U.S. Pat. No. 3,433,939 or those which undergo silver assisted cleavage to release a diffusible dye in accordance with the disclosure of U.S. Pat. No. 3,719,489; and initially nondiffusible image dye-providing materials which release a diffusible dye following coupling with an oxidized color developer as described in U.S. Pat. No. 3,227,550. The effect obtained upon any individual image dye-providing material will be dependent, at least in part, upon the distance between the compound and the image dye-providing material in the film unit.

The compounds may be incorporated into the photographic elements by any suitable technique. The compounds can be incorporated in the photographic element typically by being coated from a water or oil dispersion and the layer(s) in which they reside typically include a binder material such as gelatin or the like.

In a preferred embodiment of the invention, the compounds are utilized in diffusion transfer photographic film units in conjection with initially diffusible dye developers as the image dye-providing materials. As described in U.S. Pat. No. 2,983,606 a photosensitive element containing a dye developer and a silver halide emulsion is photoexposed annd a processing composition applied thereto, for example, by immersion, coating, spraying, flowing, etc., in the dark. The exposed photosensitive element is superposed prior to, during, or after the processing composition is applied, on a sheet-like support element which may be utilized as an image-receiving element. In a preferred embodiment, the processing composition is applied to the exposed photosensitive element in a substantially uniform layer as the photosensitive element is brought into superposed relationship with the image-receiving layer. The processing composition, positioned intermediate the photosensitive element and the image-receiving layer, permeates the emulsion to initiate development. The dye developer is immobilized or precipitated in exposed areas as a consequence of the development. In unexposed and partially exposed areas of the emulsion, the dye developer is unreacted and diffusible and thus provides an imagewise distribution of unoxidized dye developer, diffusible in the processing composition, as a function of the point-to-point degree of exposure of the silver halide emulsion. At least part of this imagewise distribution of unoxidized dye developer is transferred, by imbibition, to a superposed image-receiving layer or element, said transfer substantially excluding oxidized dye developer. The image-receiving layer receives a depthwise diffusion, from the developed emulsion, of unoxidized dye developer without appreciably disturbing the imagewise distribution thereof to provide a reversed of positive color image of the developed image. The image-receiving element may contain agents adapted to mordant or otherwise fix the diffused, unoxidized dye developer. In a preferred embodiment of said U.S. Pat. No. 2,983,606 and in certain commercial applications thereof, the desired positive image is revealed by separating the image-receiving layer from the photosensitive element at the end of a suitable imbibition period. Alternatively, as also disclosed in said U.S. Pat. No. 2,983,606, the image-receiving layer need not be separated from its superposed contact with the photosensitive element, subsequent to transfer image formation, if the support for the image-receiving layer, as well as any other layers intermediate said support and image-receiving layer, is transparent and a processing composition containing a substance, e.g. a white pigment, effective to mask the developed silver halide emulsion or emulsions is applied between the image-receiving layer and said silver halide emulsion or emulsions.

Dye developers, as noted in said U.S. Pat. No. 2,983,606, are compounds which contain, in the same molecule, both the chromophoric system of a dye and also a silver halide developing function. By "a silver halide developing function" is meant a grouping adapted to develop exposed silver halide. A preferred silver halide development function is a hydroquinonyl group. In general, the development function includes a benzenoid developing function, that is, an aromatic developing group which forms quinonoid or quinone substances when oxidized.

Multicolor images may be obtained using dye developers in diffusion transfer processes by several techniques. One such technique contemplates obtaining multicolor transfer images utilizing dye developers by employment of an integral multilayer photosensitive element, such as is disclosed in the aforementioned U.S. Pat. No. 2,983,606 and in U.S. Pat. No. 3,345,163, wherein at least two selectively sensitized photosensitive strata, superposed on a single support, are processed, simultaneously and without separation, with a single common image-receiving layer. A suitable arrangement of this type comprises a support carrying a red-sensitive silver halide emulsion stratum, a green-sensitive silver halide emulsion stratum and a blue-sensitive silver halide emulsion stratum, said emulsions having associated therewith, respectively, for example, a cyan dye developer, a magenta dye developer and a yellow dye developer. The dye developer may be utilized in the silver halide emulsion stratum, for example, in the form of particles, or it may be disposed in a stratum behind the appropriate silver halide emulsion strata. Each set of silver halide emulsion and associated dye developer strata may be separated from other sets by suitable interlayers, for example, by a layer or stratum or gelatin or polyvinyl alcohol. In certain instances, it may be desirable to incorporate a yellow filter in front of the green-sensitive emulsion and such yellow filter may be incorporated in an interlayer. However, where desirable, a yellow dye developer of the appropriate spectral characteristics and present in a state capable of functioning as a yellow filter may be so employed and a separate yellow filter omitted.

Particularly useful products for obtaining multicolor dye developer images are disclosed in U.S. Pat. No. 3,415,644. This patent discloses photographic products wherein a photosensitive element and an image-receiving element are maintained in fixed relationship prior to exposure, and this relationship is maintained as a laminate after processing and image formation. In these products, the final image is viewed through a transparent (support) element against a light-reflecting, i.e., white background. Photoexposure is made through said transparent element and application of the processing composition provides a layer of light-reflecting material to provide a white background. The light-reflecting material (referred to in said patent as an "opacifying agent") is preferably titanium dioxide, and it also performas an opacifying function, i.e., it is effective to mask the developed silver halide emulsions so that the transfer image may be viewed without interference therefrom, and it also acts to protect the photoexposed silver halide emulsions from post-exposure fogging by light passing through said transparent layer if the photoexposed film unit is removed from the camera before image-formation is completed.

U.S. Pat. No. 3,647,437 is concerned with improvements in products and processes disclosed in said U.S. Pat. No. 3,415,644, and discloses the provision of light-absorbing materials to permit such processes to be performed, outside of the camera in which photoexposure is effected, under much more intense ambient light conditions. A light-absorbing material or reagent, preferably a pH-sensitive phthalein dye, is provided so positioned and/or constituted as not to interfere with photoexposure but so positioned between the photoexposed silver halide emulsions and the transparent support during processing after photoexposure as to absorb light which otherwise might fog the photoexposed emulsions. Furthermore, the light-absorbing material is so positioned and/or constituted after processing as not to interfere with viewing the desired image shortly after said image has been formed. In the preferred embodiments, the light-absorbing material, also sometimes referred to as an optical filter agent, is initially contained in the processing composition together with a light-reflecting material, e.g., titanium dioxide. The concentration of the light-absorbing dye is selected to provide the light transmission opacity required to perform the particular process under the selected light conditions.

In a particularly useful embodiment, the light-absorbing dye is highly colored at the pH of the processing composition, e.g., 13–14, but is substantially non-absorbing of visible light at a lower pH, e.g., less than 10–12. This pH reduction may be effected by an acid-reacting reagent appropriately positioned in the film unit, e.g., in a layer between the transparent support and the image-receiving layer.

The dye developers are preferably selected for their ability to provide colors that are useful in carrying out subtractive color photography, that is, the previously mentioned cyan, magenta and yellow. The dye developers employed may be incorporated in the respective silver halide emulsion or, in the preferred embodiment, in a separate layer behind the respective silver halide emulsion, and such a layer of dye developer may be applied by use of a coating solution containing the respective dye developer distributed, in a concentration calculated to give the desired coverage of dye developer per unit area, in a film-forming natural, or synthetic, polymer, for example, gelatin, polyvinyl alcohol, and the like, adapted to be permeated by the processing composition.

Other diffusion transfer products and processes in which the dye developers of the present invention may be utilized are described in U.S. Pat. Nos. 3,573,043 and 3,594,165. For convenience, the entire disclosure of each of the six patents referred to immediately above is hereby incorporated by reference herein.

A particularly useful film unit according to the invention is one wherein the photosensitive element includes a light-reflecting layer between the silver halide layer and the image dye-providing material layer (as described in Canadian Pat. No. 668,592), the substrate of the photosensitive element carries the polymeric acid neutralizing layer which in turn carries the timing layer (as described in U.S. Pat. No. 3,573,043) and the processing composition includes an oximated polydiacetone acrylamide thickening agent (as described in U.S. Pat. No. 4,202,694).

In a preferred diffusion transfer film unit according to the invention a development restrainer precursor of the invention is incorporated in the photosensitive element in a layer between the support of the element and the silver halide emulsion closest to that support. This structure combines a delay in the cleavage of the material with a delay in the diffusion of the released development restrainer through the film unit.

In one preferred embodiment of a diffusion transfer film unit according to the invention a compound according to the invention is incorporated in the photosensitive element and the film unit is processed with a processing composition which includes 4-hydroxy phenylmercaptotetrazole.

The invention will now be described further in detail with respect to specific preferred embodiments by way of examples, it being understood that these are illustrative only and the invention is not intended to be limited to the materials, conditions, process parameters, etc. which are recited therein. All parts and percentages are by weight unless otherwise indicated.

EXAMPLE I

Preparation Of Compound I

A solution of 1.4 g. (0.010 mole) of 5-hydroxymethyl uracil in 12.5 ml. of concentrated hydrochloric acid was prepared. A colorless precipitate (5-chloromethyl uracil) formed within two minutes and after about ten minutes the precipitate was collected by filtration, washed rapidly with ice cold water, dried and then suspended in 10 ml. of dimethylformamide.

To this stirred suspension there was added a solution of 2.0 g. (0.01 mole) of 1-phenyl-1H-tetrazole-5-thiol, sodium salt in 10 ml. of dimethylformamide. The mixture was stirred at 25° C. for two hours and then quenched with 100 ml. of ice/water. The colorless solid which formed was collected by filtration, washed with water and dried in air to give 1.9 g. of crude product, m.p. 197°–200° C. (dec.).

The crude product was recrystallized from 30 ml. of methyl cellosolve. The colorless crystals which separated from the filtered and cooled liquors were collected by filtration, washed with methyl cellosolve and then with ethyl ether and dried in air to give 0.7 g. of compound I, m.p. 222°–223° C. (dec.).

$C_{12}H_{10}N_6O_2S$ requires 47.67% C; 3.33% H; 27.80% N; 10.58% O and 10.61% S. Elemental analysis found 47.73% C; 3.42% H; 27.80% N; 10.69% O and 10.54% S.

The structure of the product was confirmed by $^{13}C$ NMR and IR spectra.

EXAMPLE II

Preparation of Compound II

A suspension of 1.6 g. (0.0092 mole) of 5-chloromethyl-3-methyluracil and 2.0 g. (0.01 mole) of 1-phenyl-1H-tetrazole-5-thiol, sodium salt in 25 ml. of chilled dimethylformamide was stirred in an ice/water bath for 15 minutes. The initial suspension became a thick slurry which was then diluted with 150 ml. of ice water and filtered. The product was washed with cold water and dried in air to give 2.5 g., m.p. 215°–216° C. (dec.).

This crude product was recrystallized from 50 ml. of methyl cellosolve. The colorless crystals which separated were collected by filtration, washed sparingly with cold methyl cellosolve and then with ethyl ether and dried in air to give 2.0 g. of compound II, m.p. 219°–220° C. (dec.).

$C_{13}H_{12}N_6O_2S$ requires 49.36% C; 3.82% H; 26.57% N; 10.12% O and 10.13% S. Elemental analysis found 49.48% C; 3.89% H; 26.49% N; 9.98% O and 10.02% S.

The structure of the product was confirmed with $^{13}C$ NMR and IR spectra.

EXAMPLE III

Preparation Of Compound III

To a stirred solution of 2.0 g. (0.010 mole) of 1-phenyl-1-H-tetrazole-5-thiol, sodium salt in 10 ml. of dry dimethylformamide in an ice/salt bath under dry nitrogen there was added 5-chloromethyl-6-methyl uracil (1.75 g., 0.010 mole) and the suspension stirred vigorously for 15 minutes while allowing it to warm to room temperature. The suspension was then chilled and diluted with 50 ml. of ice-cold water. The colorless precipitate which formed was collected by filtration, washed with water and air dried to give 1.6 g. of crude product, m.p. 218°–220° C. (dec.).

The crude product was recrystallized from 20 ml. of methyl cellosolve using diatomaceous earth. The colorless crystals which separated from the filtered cooled liquors were collected by filtration, washed with methanol and then with ethyl ether and dried in air to give 1.0 g. of compound III, m.p. 239°–240° C. (dec.).

A $^{13}C$ NMR spectrum indicated that the product was contaminated with methyl cellosolve. The compound was heated at 80° C. in a vacuum oven for 4 hours.

$C_{13}H_{12}N_6O_2S$ requires 49.37% C; 3.80% H; 26.58% N; 10.13% O and 10.19% S. Elemental analysis of the product found 49.07% C; 5.01% H; 22.95% N; 14.08% O and 8.50% S.

Calculating for the product on the basis that $\frac{2}{3}$ of an equivalent of methyl cellosolve were present; $C_{45}H_{52}N_{18}O_{10}S_3$ requires 49.08% C; 4.76% H; 22.89% N; 14.53% O and 8.74% S.

EXAMPLE IV

Preparation Of Compound IV

To a stirred solution of 3.9 g (0.020 mole) of 1-(p-hydroxyphenyl)tetrazole-5-thiol in 25 ml. of dimethylformamide at 25° C. under nitrogen, there was added sodium methylate (1.1 g, 0.020 mole) and stirring continued for 15 minutes. The mixture was cooled in an ice/water bath and 5-chloromethyl uracil (3.2 g, 0.020 mole) added. The suspension was stirred for 30 minutes at 0° C. and then poured into 150 ml. of ice-cold water containing 2 ml. of glacial acetic acid. The colorless precipitate which formed was collected by filtration, washed with water and dried overnight in air to give 5.8 g of compound IV, m.p. 241°–243° C. (dec.).

$C_{12}H_{10}N_6O_3S \cdot H_2O$ requires 42.86% C; 3.57% H; 25.00% N; 19.05% O and 9.52% S. Elemental analysis found 42.75% C; 3.76% H; 25.09% N; 19.11% O and 9.43% S.

The structure of the product was confirmed with $^{13}C$ NMR and IR spectra.

EXAMPLE V

Preparation Of Compound V

To a stirred solution of 1.0 g. (0.0030 mole) of compound XI in 20 ml. of dry pyridine at −20° C. under nitrogen acetyl chloride (2 ml.) was added dropwise over a 2 minute period. A thick colorless precipitate formed. The mixture was stirred at −20° C. for 15 minutes, then at 0° C. for 1 hour and finally at room temperature for 15 minutes. The mixture was cooled to 0° C., treated with crushed ice and diluted with 100 ml. of ice cold water. The colorless solid which formed was filtered off, washed with water and dried in air to give 0.9 g. of compound V, m.p. 205°–206° C. (dec.).

$C_{15}H_{14}N_6O_4S$ requires 48.13% C; 3.74% H; 22.46% N; 17.11% O and 8.56% S. Elemental analysis found 47.81% C; 4.24% H; 22.23% N; 17.03% O and 8.51% S.

The structure of the product was confirmed by IR and $^{13}C$ NMR spectra.

EXAMPLE VI

Preparation Of Compound VI

A mixture of 1.6 g. (0.0092 mole) of 5-chloromethyl-3-methyl uracil and 2.2 g. (0.010 mole) of 2-mercapto-5-phenyl-1,3,4-oxadiazole, potassium salt in 25 ml. of dimethylformamide was stirred in an ice water bath for 30 minutes during which time a clear solution was formed and a white solid precipitated out. The mixture was diluted with 100 ml. of ice cold water and filtered. The residue was washed with cold water and dried in air to give 2.4 g. of crude product, m.p. 257°–259° C. (dec.).

The crude product was recrystallized from 50 ml. of methyl cellosolve. The colorless crystals which separated were washed sparingly with cold methyl cellosolve and then with ethyl ether and dried in air to give 1.7 g. of compound VI, m.p. 260°–264° C.

$C_{14}H_{12}N_4O_3S$ requires 53.16% C; 3.82% H; 17.71% N; 15.17% O and 10.13% S. Elemental analysis found 53.23% C; 3.93% H; 17.64% N; 15.39% O and 9.92% S.

The structure of the product was confirmed with $^{13}C$ NMR and IR spectra.

EXAMPLE VII

Preparation Of Compound VII

A mixture of 2.0 g (0.0125 mol) of 5-chloromethyl uracil and 6.0 g (0.03 mol) of 1-phenyl-1H-tetrazole-5-thiol, sodium salt in 25 ml of dimethylformamide was stirred under nitrogen at 80° C. for 6 hours. The crude mixture was poured into 150 ml of ice/water mixture and the precipitate collected by filtration, washed with water and air dried to give 2.3 g of a colorless powder, m.p. 228°–230° C. (dec.).

The crude product was recrystallized from 50 ml of methyl cellosolve. Colorless crystals separated from the filtered cooled solution after the addition of diethyl ether until a slight cloudiness occurred. The crystals were collected by filtration, washed with diethyl ether and dried in air to give 0.8 g of compound VII, m.p. 236°–237° C. (dec.).

$C_{12}H_{10}N_6O_2S$ requires 47.67% C, 3.33% H, 27.80% N, 10.58% O and 10.61% S. Elemental analysis found 47.69% C, 3.50% H, 27.63% N, 10.65% O and 10.48% S.

The structure of the product was confirmed by $^{13}C$ NMR and IR spectra.

EXAMPLE VIII

Preparation Of Compound VIII

A mixture of 1.5 g (0.0086 mol) of 5-chloromethyl-3-methyluracil and 2.0 g (0.01 mol) of 1-phenyl-1H-tetrazole-5-thiol, sodium salt in 40 ml of dry dimethylformamide was warmed on a steam bath under dry nitrogen for 25 minutes with occasional agitation. A pale yellow milky suspension formed. The mixture was poured slowly into 200 ml of a stirred ice/water mixture and the colorless solid which separated out was collected by filtration, washed with water and dried in air to give 2.5 g of crude product, m.p. 215° C. (dec.).

The crude product was recrystallized from 25 ml of methyl cellosolve to give 1.4 g of compound VIII, m.p. 223° C. (dec.).

$C_{13}H_{12}N_6O_2S$ requires 49.36% C, 3.82% H, 26.57% N, 10.12% O and 10.13% S. Elemental analysis found 49.33% C, 3.85% H, 26.47% N, 10.14% O and 10.08% S.

The structure of the product was confirmed by $^{13}C$ NMR and IR spectra.

EXAMPLE IX

Preparation Of Compound IX

A mixture of 2.0 g (0.0125 mol) of 5-chloromethyl uracil and 2.7 g (0.0125 mol) of 2-mercapto-5-phenyl-1,3,4-oxadiazole, potassium salt in 40 ml of dimethylformamide was stirred at 0°–5° C. for 30 minutes under nitrogen. The mixture was poured into 200 ml of ice water. The colorless precipitate which formed was collected by filtration, washed with water and dried in air to give 2.0 g of compound IX, m.p. 299°–300° C. (dec.).

$C_{13}H_{10}N_4O_3S$ requires 51.65% C, 3.34% H, 18.53% N, 15.88% O, and 10.61% S. Elemental analysis found 51.46% C, 3.43% H, 18.51% N, 16.06% O and 10.41% S.

The structure of the product was confirmed by $^{13}C$ NMR and IR spectra.

EXAMPLE X

Preparation Of Compound X

A mixture of 4.0 g (0.025 mol) of 5-chloromethyl uracil and 5.4 g (0.025 mol) of 2-mercapto-5-phenyl-1,3,4-oxadiazole, potassium salt in 50 ml of dimethylformamide was stirred at 25° C. for 15 minutes, followed by warming on a steam bath for 10 minutes and then poured into 200 ml of ice water. The colorless precipitate which separated out was collected by filtration, washed with water and dried in air to give 4.1 g of crude product, m.p. 294°–297° C. (dec.).

$C_{13}H_{10}N_4O_3S$ requires 51.65% C, 3.34% H, 18.53% N, 15.88% O and 10.61% S. Elemental analysis found 51.46% C, 3.43% H, 18.40% N, 15.86 O and 10.73% S.

The crude product was recrystallized from about 200 ml of methyl cellosolve to give 2.2 g of a colorless, granular solid, m.p. 304°–306° C. (dec.). The structure of the product was confirmed by $^{13}C$ NMR and IR spectra.

EXAMPLE XI

Preparation Of Compound XI

To a stirred solution of 0.3025 g (0.0056 mol) of sodium methoxide in 10 ml of methanol under nitrogen there were added 1.084 g (0.0056 mol) of 1-(4-hydroxy)- phenyl-1H-tetrazole-5-thiol. A clear gold-colored solution was formed. The system was then purged with nitrogen to dryness to give 1-(4-hydroxy)phenyl-1H-tetrazole-5-thiol, sodium salt.

About 5 ml of dimethylformamide were added to the dry sodium salt and the mixture stirred at room temperature followed by the addition of 0.9762 g (0.0056 mol) of 5-chloromethyl-3-methyluracil and stirring for 1 hour. The cloudy solution was cooled in an ice water bath and about 25 ml of ice cold water added to it. The white solid which formed was collected by filtration, washed with ice cold water and dried to give 1.3 g of crude product, m.p. 219°–220° C. (dec.).

About 25 ml. of 2-methoxyethanol were heated to boiling and added to a cool flask containing the crude product. The flask was then heated on a hot plate. The white milky solution which formed initially turned to a transparent gold color as heating continued. The solution was filtered and white crystals began to form in the gold colored filtrate. The filtrate was allowed to stand at room temperature for a period of time and then cooled in an ice/salt bath to facilitate crystal formation. The crystals were collected, washed with 2-methoxyethanol and then with ether and dried to give 0.6 g of a fine crystalline solid, compound XI, m.p. 230°–234° C.

$C_{13}H_{12}N_6O_3S$ requires 46.98% C, 3.64% H, 25.29% N, 14.44% O and 9.65% S. Elemental analysis found 47.09% C, 3.67% H, 25.37% N, 14.20% O and 9.69% S.

The structure of the product was confirmed by $^{13}C$ NMR and IR spectra.

EXAMPLE XII

Preparation Of Compound XII

In a dry nitrogen atmosphere 1.0 g (0.0033 mol) of compound I was added to a mixture of 3 ml of benzoyl bromide in 10 ml of dry pyridine at 0°–5° C. The resulting yellow suspension was stirred at 0° C. for 1 hour and then for an additional hour during which the temperature was allowed to rise to 25° C. The pyridine was evaporated off in a stream of nitrogen and the yellow residue triturated with 20 ml of cold water which was decanted off. The clear oily residue gradually crystallized on standing for about 10 days.

The crude product was recrystallized from 30 ml of 2-propanol. The colorless crystals which formed were collected by filtration, washed with diethyl ether and dried in air to give 0.5 g of compound XII, m.p. 269°–270° C. (dec.).

$C_{19}H_{14}N_6O_3S$ requires 56.15% C, 3.47% H, 20.68% N, 11.81% O and 7.89% S. Elemental analysis found 56.07% C, 3.60% H, 20.55% N, 11.99% O and 7.97% S.

The structure of the product was confirmed by $^{13}C$ NMR and IR spectra.

EXAMPLE XIII

Preparation Of Compound XIII

A mixture of 0.54 g (0.01 mol) of sodium methoxide in 20 ml of methanol was stirred at room temperature for about 10 minutes until a semi-clear solution was formed and nitrogen gas then passed over the solution. The solution was then kept stoppered in a flask.

To this solution then were added 1.84 g (0.01 mol) of 2-mercapto-5-(2'-thienyl)-1,3,4-oxadiazole resulting in a clear pale gold colored solution. The methanol was evaporated off to leave a gummy yellow residue which was dissolved in 20 ml of dimethylformamide to give a semi-clear pale gold colored solution. To this solution there were added 1.61 g (0.01 mol) of 5-chloromethyl uracil and the reaction allowed to continue for about 20 minutes at 0° C. until a thick white fluffy suspension was formed. The suspension was poured into ice water and the solid collected by filtration and allowed to dry in air.

The crude product was added to 70 ml of methyl cellosolve, the mixture heated to boiling and then filtered.

The filtrate was cooled in an ice/water bath and the resulting solid collected by filtration, washed with a small volume of methyl cellosolve and then a larger volume of ether and then dried in air to give 1.2 g of compound XIII, m.p. 286°–291° C.

$C_{11}H_8N_4O_3S_2$ requires 42.85% C, 2.62% H, 18.17% N, 15.57% O and 20.80% S. Elemental analysis found 42.89% C, 2.63% H, 18.10% N, 15.66% O and 20.70% S.

The structure of the product was confirmed by $^{13}C$ NMR and IR spectra.

EXAMPLE XIV

Preparation Of Compound XIV

A clear solution was formed by adding 0.59 g (0.01 mol) of sodium methoxide to 20 ml of methanol and stirring for about 7 minutes. Nitrogen gas was passed over the solution and it was kept stoppered. To the solution there were added 1.19 g (0.0065 mol) of 2-mercapto-5-(2'-thienyl)-1,3,4-oxadiazole and the methanol then removed by evaporation to give a gummy residue. To the residue there were added 1.61 g (0.01 mol) of 5-chloromethyl uracil and 20 ml of dimethylformamide and the mixture stirred. The resulting solution was allowed to stand overnight, heated on a steam bath for about 15 minutes and poured into ice water. The resulting crystals were collected by filtration and dried to give 2.0 g of crude product.

The crude product was added to 40 ml of methyl cellosolve and the mixture heated to boiling. A portion of the product went into solution. The suspension was filtered and the filtrate placed in a freezer. The solid portion was dried to give 0.7 g of product, m.p. 291°–294° C. The precipitate which formed in the filtrate on standing was collected and dried to give 0.4 g of product, m.p. 289°–292° C. IR spectra showed the two materials to be essentially the same.

$C_{11}H_8N_4O_3S_2$ requires 42.85% C, 2.62% H, 18.17% N, 15.57% O and 20.80% S. Elemental analysis found 43.04% C, 2.79% H, 18.19% N, 18.19% O and 18.00% S.

The structure of the product was confirmed by $^{13}C$ NMR and IR spectra.

EXAMPLE XV

Preparation Of Compound XV

To a solution of 2-benzothiazolethiol, sodium salt (from 1.67 g (0.01 mol) of 2-benzothiazolethiol) in 20 ml of dimethylformamide there were added 1.61 g (0.01 mol) of 5-chloromethyl uracil. The milky white solution which formed was stoppered and allowed to stand overnight. The solution was then heated for 30 minutes and subsequently poured into 150 ml. of ice water. White crystals formed giving the solution an overall white milky color. The solution was filtered and the product washed with ice water to give a white, pasty product.

About 40 ml of methyl cellosolve were added to the pasty product and the mixture heated with stirring until boiling. The milky white suspension was filtered hot to give a clearer pale yellow solution which was again heated. Diatomaceous earth was added to the solution to remove any further impurities. The transparent gold colored solution was allowed to stand in a freezer overnight. Ether was added to the solution and it was poured into an ice bath. The crystals which had formed were collected by filtration, washed with ether and allowed to dry to give 1.1 g of compound XV, m.p. 290°–300° C.

$C_{12}H_9N_3O_2S_2$ requires 49.48% C, 3.09% H, 14.43% N, 11.00% O and 21.99% S. Elemental analysis found 49.40% C, 3.56% H, 14.16% N, 11.33% O and 21.68% S.

The structure of the product was confirmed by $^{13}C$ NMR and IR spectra.

EXAMPLE XVI

Preparation Of Compound XVI

A mixture of 1.08 g (0.0199 mol) of sodium methoxide in 40 ml of methanol was stirred under nitrogen at room temperature for about 10 minutes and then there were added 3.02 g (0.0199 mol) of 2-mercaptobenzoxazole. Charcoal was added to the resulting dark brown solution which was then stirred for 10 minutes. The solution was filtered and the dark gold colored filtrate placed on a rotary evaporator to remove the methanol leaving behind a gold solid. The gold solid was dissolved in 25 ml of dimethylformamide and to the solution there were added 3.22 g (0.02 mol) of 5-chloromethyl uracil. The resulting cloudy white mixture was stirred, placed on a steam bath for 10 minutes (the color changed to tan) and poured into ice water where white crystals formed.

The crystals were collected, dried and then added to a solution of 2 parts of methylcellosolve and 1 part of water. After heating for about 5 minutes a semi-clear solution formed. The resulting crystals were collected by filtration and dried to give 1.7 g of compound XVI, m.p. 310°–313° C.

$C_{12}H_9N_3O_3S$ requires 52.36% C, 3.27% H, 15.27% N, 17.45% O and 11.64% S. Elemental analysis found 52.38% C, 3.33% H. 15.26% N, 17.26% O and 11.77% S.

The structure of the product was confirmed by $^{13}C$ NMR and IR spectra.

EXAMPLE XVII

Preparation Of Compound XVII

To a solution of 0.54 g (0.01 mol) of sodium methoxide in 20 ml of methanol (formed as in Example XVI) there were added 1.70 g of 6-mercaptopurine monohydrate. The solution turned a cloudy yellow color. After the methanol was removed by evaporation 10 ml of dimethylformamide were added and a golden brown cloudy solution was formed. To the solution there were added 1.61 g (0.01 mol) of 5-chloromethyl uracil (the solution turned milky white) and after about 15 minutes the solution was poured into ice water. The resulting white solid was collected by filtration and allowed to dry in air to give 2.6 g of compound XVII, m.p. 283°–286° C.

$C_{10}H_8N_6O_2S.H_2O$ requires 40.81% C, 3.42% H, 28.56% N, 16.31% O and 10.89% S. Elemental analysis found 40.83% C, 3.27% H, 28.60% N, 16.12% O and 11.01% S.

The structure of the product was confirmed by $^{13}C$ NMR and IR spectra.

EXAMPLE XVIII

Preparation Of Compound XVIII

To a solution of 0.54 g of sodium methoxide in 20 ml of methanol (formed as in Example XVI) there were added 1.12 g (0.01 mol) of 2-mercaptopyrimidine resulting in a cloudy bright lime-gold colored mixture. The mixture was heated on a steam bath until almost all of the methanol had evaporated and then 20 ml of dimethylformamide were added. The resultant reddish-yellow solution was stirred at room temperature for about 5 minutes and then 1.61 g (0.01 mol) of 5-chloromethyl uracil were added. The resulting milky yellow solution was allowed to stir overnight at room temperature. The solution was then heated on a steam bath for 5 minutes, stirred briefly and ice water added. The resulting white solid was collected by filtration and allowed to dry in air to give 2.2 g of product, m.p. 271°–276° C.

To the crude product there were added 35 ml of glacial acetic acid and the mixture stirred and heated to boiling. The solution was then filtered. A light yellow solid began to form in the filtrate. A portion of the solid remained on the filter paper.

The solid in the filtrate was collected by filtration to give 0.6 g of product. The liquors from the latter filtration were found to contain additional solid which was collected by filtration to give 0.1 g of product. Both amounts of product were combined and washed with ether. The solid which had remained on the filter paper was added to the liquors from the last filtration, the mixture heated with stirring until it boiled and then filtered to collect the solid to give 0.2 g of product.

The three samples were combined to give 0.9 g of compound XVIII, m.p. 276°–281° C.

$C_9H_8N_4O_2S$ requires 45.76% C, 3.39% H, 23.73% N, 13.56% O and 13.56% S. Elemental analysis found 45.74% C, 3.44% H, 23.65% N, 13.70% O and 13.60% S.

The structure of the product was confirmed by $^{13}C$ NMR and IR spectra.

EXAMPLE XIX

Preparation Of Compound XIX

A solution of 158.6 mg (0.5 mmole) of a compound represented by the formula

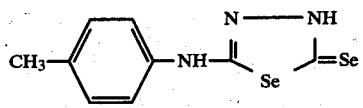

in 1 ml of anhydrous dimethylformamide was filtered through diatomaceous earth into a stirred suspension of 27.0 mg (0.5 mmole) of sodium methoxide in 1 ml of anhydrous dimethylformamide. The diatomaceous earth was washed with an additional 1 ml of anhydrous dimethylformamide which was also added to the stirred suspension. Stirring was continued under nitrogen (the complete reaction was run under nitrogen) for 30 minutes. An orange-yellow solution (without any suspended solid) was formed. This solution was syringed dropwise into a stirred solution of 80.3 mg (0.5 mmole) of 5-chloromethyl uracil in 2 ml of anhydrous dimethylformamide at 0° C. in an ice bath over a period of about 10 minutes. Stirring at 0° C. was continued for an additional 5 minutes after which the reaction mixture was added dropwise to about 40 ml of deaerated water. The resulting solid was collected by filtration, washed thoroughly in water and dried under vacuum to give 192.0 mg of a pale yellow solid, compound XIX, m.p. 230°–232° C. (dec.).

$C_{14}H_{13}N_5O_2Se_2.\frac{1}{2}H_2O$ requires 37.35% C, 3.13% H, 15.56% N, 8.88% O and 35.08% Se. Elemental analysis found 37.64% C, 3.21% H, 15.30% N, 8.71% O and 34.81% Se.

The structure of the product was confirmed by $^{13}C$ NMR and IR spectra.

EXAMPLE XX

Preparation Of Compound XX

To a solution of 2.0 g (0.006 mol) of compound IV in 25 ml of dry pyridine, stirred at −20° C. a dry ice/acetone bath under nitrogen, there were added dropwise over a 5 minute period 3 ml of acetyl chloride. A colorless precipitate formed. The mixture was stirred at <20° C. for 15 minutes and then at 0° C. for 1 hour and finally at room temperature for 45 minutes. The mixture was treated with crushed ice and then with 100 ml of ice cold water and filtered. The residue was washed well with water and dried in air to give 1.9 g of a colorless powder, m.p. 236°–237° (dec.).

The crude product was recrystallized from 125 ml of methyl cellosolve and air dried to give 1.1 g of compound XX, m.p. 243°–244° C. (dec.).

$C_{14}H_{12}N_6O_4S$ requires 46.67% C, 3.33% H, 23.33% N, 17.78% O and 8.89% S. Elemental analysis found 46.50% C, 3.44% H, 23.26% N, 17.96% O and 9.12% S.

The structure of the product was confirmed by $^{13}C$ NMR and Ir spectra.

EXAMPLE XXI

Preparation Of Compound XXI

To a vigorously stirred suspension of 1.25 g (0.01 mol) of finely divided $Na_2Se$ in 25 ml of dry dimethylformamide (which had been purged with nitrogen) there were added 1.7 g (0.01 mol) of 2-chlorobenzothiazole. The mixture was stirred under dry nitrogen at 100°–110° C. for 1 hour. A slight lightening in physical appearance occurred. The mixture was cooled in an ice/salt bath and stirred vigorously while 1.6 g (0.01 mol) of 5-chloromethyl uracil were added and the resulting mixture stirred vigorously for an additional 15 minutes during which time first a light green suspension formed which changed rapidly to a pale pink color.

The mixture was poured into 150 ml of ice/water and a pale pink solid separated out. The solid was collected by filtration, washed with water, then suspended in 100 ml of methanol and collected again by filtration. The solid was dried overnight in a vacuum desiccator to give 2.6 g of an almost colorless powder, m.p. 266°–267° C. (dec.).

The crude product (1.0 g) was dissolved in 20 ml of methyl cellosolve and 20 ml of hot 2-propanol were added. The turbid solution was filtered through diatomaceous earth. The resulting pale yellow filtrate was refrigerated over the weekend. The pale yellow crystals which separated out were collected by filtration, washed with 2-propanol and dried in air to give 0.4 g of compound XXI, m.p. 264°–265° C. (dec.).

$C_{12}H_9N_3O_2S$ Se requires 42.60% C, 2.66% H, 12.43% N, 9.47% O, 9.47% S and 23.37% Se. Elemental analysis found 42.99% C, 3.14% H, 12.26% N, 9.32% O, 9.20% S and 23.06% Se.

The structure of the product was confirmed by Ir and $^{13}C$ NMR spectra.

EXAMPLE XXII

Preparation Of Compound XXII

To a vigorously stirred suspension of 1.25 g (0.01 mol) of finely divided $Na_2Se$ in 25 ml of dry dimethylformamide (which had been purged with nitrogen) there were added 1.8 g (0.01 mol) of 5-chloro-1-phenyl-1H-tetrazole and the mixture stirred under dry nitrogen at 100°–110° C. for 1 hour during which time some lightening occurred. The mixture was cooled, with stirring under nitrogen, in an ice/salt bath and 1.6 g (0.01 mol) of 5-chloromethyl uracil added. The resulting pale yellow suspension was stirred for 15 minutes and poured into 150 ml of ice/water containing 2 ml of acetic acid. The yellow solid which formed was collected by filtration, washed with water and then with methanol and dried overnight in a vacuum desiccator to give 2.4 g of a yellow powder, compound XXII, m.p. 180°–181° C. (dec.).

$C_{12}H_{10}N_6O_2Se.\frac{1}{8}H_2O$ reqquires 41.00% C, 2.94% H, 23.91% N, 9.67% O and 22.47% Se. Elemental analysis found 40.84% C, 3.18% H, 23.74% N, 9.72% O and 22.48% Se.

The structure of the product was confirmed by IR and $^{13}C$ NMR spectra.

EXAMPLE XXIII

Preparation Of Compound XXIII

To a solution of 3.0 g (0.015 mol) of 1-(4-hydroxy)phenyl-1H-tetrazole-5-thiol in 30 ml of dimethylformamide there was added 0.84 g (0.015 mol) of sodium methylate and the mixture warmed slightly and stirred under nitrogen for 5 minutes. The pale yellow solution was stirred at 0° C. under nitrogen and to it there were added 2.7 g (0.015 mol) of 5-chloromethyl-6-methyluracil. A solution was formed almost immediately. The solution was stirred in an ice bath for 10 minutes and then poured into 150 ml of ice cold water containing 1 ml of acetic acid. The colorless solid which separated out was collected by filtration, washed with water and dried in air to give 4.1 g of compound XXIII, m.p. 238°–240° C. (dec.).

$C_{13}H_{12}N_6O_3S.\frac{3}{4}H_2O$ requires 45.15% C, 3.91% H, 24.32% N, 17.37% O and 9.26% S. Elemental analysis found 45.06% C, 4.03% H, 24.17% N, 17.54% O and 9.38% S.

The structure of the product was confirmed by IR and $^{13}C$ NMR spectra.

EXAMPLE XXIV

Preparation Of Compound XXIV

A mixture of 0.537 g (0.003 mol) of 1-(3-pyridyl)-1H-tetrazole-5-thiol and 0.162 g (0.003 mol) of sodium methylate in 10 ml of dimethylformamide was stirred under dry nitrogen at 50° C. for 5 minutes. The resulting yellow solution was stirred in an ice/salt bath under dry nitrogen and to it was added 0.4818 g (0.003 mol) of 5-chloromethyl uracil. The mixture was stirred for 45 minutes at 0°–5° C. and then treated with 50 ml of ice/water containing 0.5 ml of acetic acid. The colorless suspension was filtered, washed with water and dried in air to give 0.80 g of compound XXIV, m.p. 212°–213° C. (dec.).

$C_{11}H_9N_7O_2S$ requires 43.56% C, 2.97% H, 32.34% N, 10.56% O and 10.56% S. Elemental analysis found 43.41% C, 3.10% H, 32.12% N, 10.71% O and 10.53% S.

The structure of the product was confirmed by IR and $^{13}C$ NMR spectra.

EXAMPLE XXV

Preparation Of Compound XXV

A mixture of 2.35 g (0.01 mol) of 1-(4-acetyloxime)phenyl-1H-tetrazole-5-thiol in 25 ml of dimethylformamide was stirred at 25° C. under nitrogen and to the resulting pale yellow solution there was added 0.54 g (0.01 mol) of sodium methylate. An intense red solution was formed. The solution was cooled in an ice/salt bath and 1.60 g (0.01 mol) of 5-chloromethyl uracil were added. The resulting orange slurry was stirred in the bath under nitrogen for ½ hour during which time it became pale yellow. The solution was poured into 125 ml of ice/water containing 1 ml of acetic acid and the resulting pale yellow solid collected by filtration, washed with water and dried in air to give 3.2 g of crude product, m.p. 234°–235° C. (dec.).

The crude product was stirred in 50 ml of hot methanol, cooled, and the mixture filtered. The pale yellow solid was washed with methanol and then with diethyl ether and dried in air to give 2.4 g of compound XXV, m.p. 237°–238° C. (dec.).

$C_{14}H_{13}N_7O_3S$ requires 46.80% C, 3.62% H, 27.30% N, 13.37% O and 8.91% S. Elemental analysis found 46.72% C, 3.74% H, 27.19% N, 13.41% O and 8.87% S.

IR and $^{13}C$ NMR spectra confirmed the structure of the product.

EXAMPLE XXVI

Preparation Of Compound XXVI

To a stirred solution of 2.35 g (0.01 mol) of 1-(4-acetyloxime)phenyl-1H-tetrazole-5-thiol in 25 ml of dimethylformamide at 25° C. under nitrogen there was added 0.54 g (0.01 mol) of sodium methylate. The resulting red solution was cooled in an ice/salt bath and 1.75 g (0.01 mol) of 5-chloromethyl-3-methyluracil added to it. The resulting cloudy orange solution was stirred for 30 minutes in the bath under nitrogen and then poured into 150 ml of ice/water containing 1 ml of acetic acid with rapid stirring. The pale yellow solid which separated out was collected by filtration, washed with water and dried in air to give 3.3 g of crude product, m.p. 201°–203° C. (dec.).

The crude product was recrystallized from 80 ml of 3:1 (V/V) 2-propanol/methyl cellosolve. The pale yellow crystals were collected by filtration, washed with methanol and then with diethyl ether and dried in air to give 2.0 g of compound XXVI, m.p. 207°–208° C. (dec.).

$C_{15}H_{15}N_7O_3S$ requires 48.26% C, 4.02% H, 26.27% N, 12.87% O and 8.58% S. Elemental analysis found 48.32% C, 4.05% H, 26.28% N, 12.70% O and 8.62% S.

The structure of the product was confirmed by IR and $^{13}C$ NMR spectra.

EXAMPLE XXVII

Preparation Of Compound XXVII

To a vigorously stirred suspension of 1.25 g (0.01 mol) of finely divided $Na_2Se$ in 25 ml of dimethylformamide (previously purged with dry nitrogen) there were added 1.53 g (0.01 mol) of 2-chlorobenzoxazole and the mixture stirred under nitrogen at 108°–110° C. for 1 hour during which time the mixture became dark. The mixture was then stirred in an ice/salt bath for 15 minutes in the presence of 1.60 g (0.01 mol) of 5-chloromethyl uracil and then poured into 100 ml of ice water. The resulting gray precipitate was collected by filtration, washed successively with distilled water, methanol and diethylether and dried in air in subdued light. The crude product was dissolved in 25 ml. of dry dimethylsulfoxide and then filtered through diatomaceous earth. The yellow filtrate was poured into 100 ml of ice water and the resulting precipitate collected, washed successively with water, methanol and diethyl ether and dried in air to give a pale yellow powder, Compound XXVII, m.p. 285°–286° C. (dec.).

$C_{12}H_9N_3O_3Se\cdot\frac{1}{2}H_2O$ requires 43.50% C, 3.02% H, 12.68% N, 16.92% O and 23.86% Se. Elemental analysis found 44.72% C, 2.80% H, 13.04% N, 14.91% O and 24.53% Se.

The structure of the product was confirmed by IR and $^{13}C$ NMR spectra.

EXAMPLE XXVIII

Preparation Of Compound XXVIII

A mixture of 3.9 g (0.015 mol) of 1-(4-parasulfonamido)-phenyl-1H-tetrazole-5-thiol and 0.80 g (0.015 mol) of sodium methylate in 40 ml of dimethylformamide was stirred under dry nitrogen at 25° C. for 5 minutes during which time some heat evolved. The mixture was cooled in an ice/salt bath and 2.50 g (0.015 mol) of 5-chloromethyluracil were added. The mixture was stirred vigorously for 15 minutes and poured into 200 ml of ice/water containing 1 ml of acetic acid. The colorless precipitate which formed was collected by filtration, washed with water and then slurried with 100 ml of methanol. The precipitate was again collected, washed with methanol and then diethyl ether and air dried to give 5.2 g of compound XXVIII m.p. 255° C. (dec.).

$C_{12}H_{11}N_7O_4S_2$ requires 37.80% C, 2.89% H, 25.72% N, 16.80% O and 16.80% S. Elemental analysis found 37.73% C, 3.06% H, 25.69% N, 16.86% O and 16.70% S.

The structure of the product was confirmed by IR and $^{13}C$ NMR spectra.

EXAMPLE XXIX

Preparation Of Compound XXIX

To a solution of 3.9 g (0.015 mol) of 1-(4-parasulfonamido)-phenyl-1H-tetrazole-5-thiol in 50 ml of dimethylformamide at 25° C. under dry nitrogen there was added 0.8 g (0.015 mol) of sodium methylate. The solution was warmed slightly (it became dark) and then cooled in an ice/salt bath. To the solution there were then added, with vigorous stirring, 2.6 g (0.015 mol) of 5-chloromethyl-3-methyluracil. The color disappeared immediately and a milky mixture was formed. The mixture was stirred at 0° C. for 15 minutes and poured into 200 ml of ice/water containing 1 ml of acetic acid. The finely divided colorless precipitate which formed was collected by filtration, washed with water, resuspended in 100 ml of methanol, collected again, washed with methanol and then with diethyl ether and dried in air to give 5.9 g of compound XXIX, m.p. 220°–221° C. (dec.).

$C_{13}H_{13}N_7O_4S_2$ requires 39.49% C, 3.29% H, 24.81% N, 16.20% O and 16.20.% S. Elemental analysis found 39.44% C, 3.37% H, 24.70% N, 16.37% O and 16.33% S.

The structure of the product was confirmed by IR and $^{13}C$ NMR spectra.

EXAMPLE XXX

Preparation Of Compound XXX

A suspension of 1.25 g (0.010 mol) of $Na_2Se$ powder in 25 ml of dry dimethylformamide was stirred vigorously and to it there were added 1.8 g (0.010 mol) of 5-chloro-1-phenyl-1H-tetrazole. The mixture was stirred for 1 hour under dry nitrogen (it became dark) and then cooled in an ice/salt bath and 1.75 g of 5-chloromethyl-3-methyluracil added. The mixture was stirred in the bath for 15 minutes and then poured into 150 ml of ice/water containing 2 ml of acetic acid. The light gray precipitate which formed was collected, washed with water and dissolved in 75 ml of hot methyl cellosolve. The insoluble gray material was filtered off through diatomaceous earth and the yellow filtrate cooled in an ice/salt bath under nitrogen. The pale yellow crystals which separated were collected, washed with methyl cellosolve and then with methanol and dried to give 1.6 g of compound XXX, m.p. 187°–188° C. (dec.).

$C_{13}H_{12}N_6O_2Se$ requires 42.98% C, 3.31% H, 23.14% N, 8.82% O and 21.76% Se. Elemental analysis found 43.11% C, 3.48% H, 22.98% N, 8.90% O and 21.73% Se.

The structure of the product was confirmed by IR and $^{13}C$ NMR spectra.

EXAMPLE XXXI Preparation Of Compound XXXI

A mixture of 1.5 g of crude compound I in 10 ml of acetic anhydride was heated to reflux and 3 drops of $H_2SO_4$ added to it. A solution formed within one minute. The solution was refluxed for 15 minutes, then cooled to room temperature and allowed to stand in a stopped flask for 3 hours. The solution was poured into 100 ml of ice water and a gummy material separated out. The liquors were decanted and fresh ice water added twice. The gum crystallized and was collected, washed with water and dried in air to give an off-white powder. The crude product was recrystallized from 2-propanol to give a light tan powder compound XXXI, m.p. 172°–179° C. (dec.).

$C_{14}H_{12}N_6O_3S$ requires 48.84% C, 3.49% H, 24.42% N, 13.95% O and 9.30% S. Elemental analysis found 48.79% C, 3.70% H, 24.31% N, 14.05% O and 9.21% S.

The structure of the product was confirmed by $^{13}C$ NMR and IR spectra.

EXAMPLE XXXII

Preparation Of Compound XXXII

A solution of 1.0 g (0.003 mol) of compound XI and 0.53 g (0.003 mol) of 2-(methylsulfonyl)ethyl chloroformate in 20 ml of pyridine was stirred for 1½ hours under dry nitrogen and then added dropwise to 200 ml of rapidly stirred ice water. The solution was filtered and a very fine white solid formed in the filtrate. The solid was recovered by filtration, washed repeatedly with cold water and then with methanol and dried in air. The crude product was recrystallized from 30 ml of methanol, washed with methanol and ether and dried in air to give 0.5 g of compound XXXII, m.p. 162°–153° C.

$C_{17}H_{18}N_6O_7S$ requires 42.32% C, 3.72% H, 17.43% N, 13.28% S and 23.24% O. Elemental analysis found 41.99% C, 3.97% H, 17.33% N, 13.65% S and 22.99% O.

The structure of the product was confirmed by an IR spectrum.

EXAMPLE XXXIII

Preparation Of Compound XXXIII

A solution of 3 g (0.0117 mol) of 1-(4-parasulfonamido)phenyl-1H-tetrazole-5-thiol and 0.63 g (0.0117 mol) of sodium methylate in 15 ml of dimethylformamide was stirred under nitrogen for 20 minutes at 40° C., then cooled to 0° C. and 2.66 g (0.0117 mol) of 5-chloromethyl-6-methyluracil added to it. The solution was stirred under nitrogen at 0° C. for 15 minutes and then poured into 100 ml of ice water to which 1 ml of acetic acid had been added. The white precipitate was collected by filtration, washed successively with cold water, methanol and diethyl ether and dried in air. The crude product was slurried in methanol, filtered, washed successively with methanol and ether and dried in air to give 3.9 g of Compound XXXIII, m.p. 248° C. (dec.).

$C_{13}H_{13}N_7S_2O_4$ requires 39.49% C, 3.29% H, 24.81% N, 16.20% O and 16.20% S. Elemental analyis found 39.35% C, 3.40% H, 24.74% N, 16.17% O and 16.48% S.

The structure of the product was confirmed by IR and $^{13}C$ NMR spectra.

EXAMPLE XXXIV

Preparation Of Compound XXXIV

A solution of 5 g (0.033 mol) of 2-benzimidazolethiol and 1.8 g (0.033 mol) of sodium methylate in 30 ml of dimethylformamide was warmed under nitrogen, then cooled to 0° C. and 5.34 g (0.033 mol) of 5-chloromethyluracil added to it. The solution was stirred under nitrogen at 0° C. for 20–25 minutes and then poured into 200 ml of ice water to which 2 ml of acetic acid had been added. A flaky off-white precipitate formed, which on filtering, turned gummy. The fine white precipitate which formed in the filtrate was collected, washed with cold water and dried in air. The crude product was slurried in methanol, collected, washed and dried in air to give 3.2 g of compound XXXIV, m.p. 325°–328° C.

$C_{12}H_9N_4O_2S$ requires 52.75% C, 3.30% H, 20.51% N, 11.72% O and 11.72% S. Elemental analysis found 52.41% C, 3.76% H, 20.38% N, 11.77% O and 11.89% S.

The structure of the product was confirmed by an IR spectrum.

EXAMPLE XXXV

As a control a film unit was prepared as follows: the negative element comprises an opaque subcoated polyethylene terephthalate film base on which the following layers were coated in succession:

1. as a polymeric acid layer approximately 9 parts of a ½ butyl ester of polyethylene/maleic anhydride copolymer and 1 part of polyvinyl butyral coated at a coverage of about 26,460 mgs./m.$^2$;
2. a timing layer comprising about 97% of a 60-29-6-4-0.4 pentapolymer of butylacrylate, diacetone acrylamide, methacrylic acid, styrene and acrylic acid and about 3% polyvinylalcohol coated at a coverage of about 3000 mgs./m.²;

3. a cyan dye developer layer comprising about 511 mgs/m² of a cyan developer represented by the formula

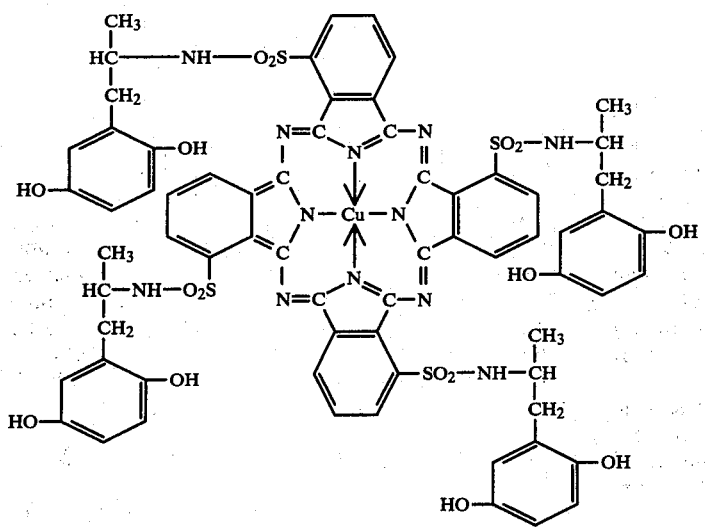

about 70 mgs/m² of 4'-methyl phenyl hydroquinone and about 317 mgs/m² of gelatin;

4. a red-sensitive silver iodobromide emulsion layer comprising about 1378 mgs.m.² of silver and about 827 mgs./m.² of gelatin;

5. an interlayer comprising about 2090 mgs./m.² of the pentapolymer described in layer 2, about 110 mgs./m.² of polyacrylamide and about 44 mgs./m.² of succinaldehyde;

6. a magenta dye developer layer comprising about 460 mgs./m.² of a magenta dye developer represented by the formula

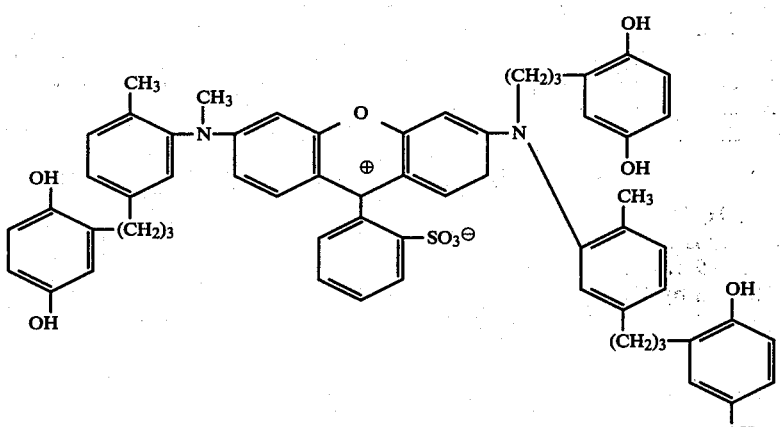

and about 210 mgs/m² of gelatin;

7. a green-sensitive silver iodobromide emulsion layer comprising about 723 mgs/m² of silver and about 318 mgs/m² of gelatin;

8. an interlayer comprising about 1881 mgs/m² of the pentapolymer described in layer 2 and about 99 mgs/m² of polyacrylamide;

9. a yellow dye developer layer comprising about 689 mgs/m² of a yellow dye developer represented by the formula

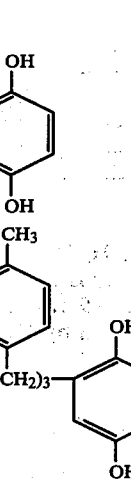

and about 265 mgs/m² of gelatin;

10. a blue-sensitive silver iodobromide emulsion layer comprising about 764 mgs/m² of silver, about 499 mgs/m² of gelatin and about 265 mgs/m² of 4-methyl phenyl hydroquinone;

11. a gelatin layer coated at a coverage of about 400 mgs/m²; and 12. a topcoat layer coated at a coverage of about 20 mgs/ft² (215 mgs/m²) of gelatin.

The image-receiving element comprised a transparent subcoated polyethylene terephthalate film base upon which there was coated an image-receiving layer coated at a coverage of about 300 mgs/ft² (3229 mgs/m²) of a graft copolymer comprised of 4-vinylpyridene (4VP) and vinyl benzyl trimethyl ammonium chloride (TMQ) grafted onto hydroxyethyl cellulose (HEC) at a ration HEC/4VP/TMQ of 2.2/2.2/1; and about 5 mgs/ft² (53.8 mgs/m²) of 1,4-butanediol diglycidyl ether.

The film unit was processed with a processing composition made up as follows:

| | |
|---|---|
| Water | 1632 ml. |
| $TiO_2$ | 2312.0 grams |
| Oximated polydiacetone acrylamide | 32.0 grams |
| Potassium hydroxide (45% solution) | 468.0 grams |
| Benzotriazole | 22.0 grams |
| 4-aminopyrazolo-(3,4-d)pyrimidine | 10.0 grams |
| 6-methyl uracil | 12.0 grams |
| N—hydroxyethyl-N,N′,N′—triscarboxymethyl ethylene diamine | 30.0 grams |
| Polyethylene glycol (M.W. 4000) | 18.0 grams |
| Bis(2-aminoethyl)sulfide | 0.8 grams |
| Colloidal silica (30% solids) | 37.0 grams |
| N—phenethyl-α-picolinium bromide (50% solids) | 102.0 grams |
| Allopurinol | 3.3 grams |
| 2-methyl imidazole | 23.8 grams |
| 6-methyl-5-bromo azabenzimidazole | 4.8 grams |
| 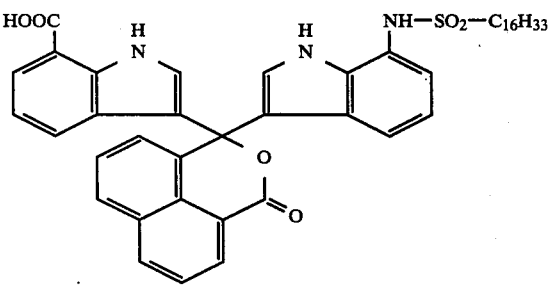 | 14.0 grams |
| 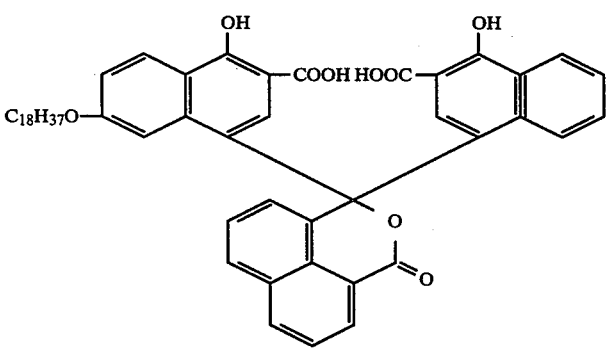 | 62.3 grams |

The negative element was exposed (2-meter-candle-seconds) on a sensitometer to a test exposure scale with white light, and then brought together with the image receiving element and processed at room temperature (24° C.) by passing the film unit through a pair of rollers set at a gap spacing of about 0.0026 inch. The film unit was kept intact and viewed through the base of the image receiving element.

Identical film units were processed in the same manner at 7° C. and 35° C. respectively. The neutral density columns of the images were read on a densitometer to obtain the $D_{max}$ and $D_{min}$ values for red, green and blue respectively. The values obtained are shown in Table II.

Two film units according to the invention were prepared. These were identical to the control with the exception that in one (Film Unit XXXVA) the negative further included about 20 mgs/ft² (215 mgs/m²) of compound IV in the topcoat layer and in the other (Film Unit XXXVB) the negative further included 20 mgs/ft² of compound XI in the topcoat layer. The film units were processed as described above at 7° C., 24° C. and 35° C. The results obtained are shown in Table II.

TABLE II

| | 7° C. | | | | | |
|---|---|---|---|---|---|---|
| FILM | Dmax | | | Dmin | | |
| UNIT | R | G | B | R | G | B |
| Control | 1.48 | 1.79 | 1.92 | 0.17 | 0.15 | 0.19 |
| XXXVA | 1.19 | 1.57 | 1.95 | 0.18 | 0.16 | 0.18 |
| XXXVB | 1.31 | 1.67 | 1.91 | 0.18 | 0.15 | 0.17 |
| | 24° C. | | | | | |
| | Dmax | | | Dmin | | |
| | R | G | B | R | G | B |
| Control | 1.59 | 1.50 | 1.38 | 0.16 | 0.14 | 0.16 |
| XXXVA | 1.45 | 1.58 | 1.64 | 0.18 | 0.16 | 0.18 |
| XXXVB | 1.60 | 1.49 | 1.40 | 0.18 | 0.15 | 0.17 |
| | 35° C. | | | | | |

TABLE II-continued

| FILM | Dmax | | | Dmin | | |
|---|---|---|---|---|---|---|
| UNIT | R | G | B | R | G | B |
| Control | 1.38 | 1.21 | 1.12 | 0.16 | 0.14 | 0.17 |
| XXXVA | 1.42 | 1.40 | 1.41 | 0.17 | 0.16 | 0.20 |
| XXXVB | 1.53 | 1.30 | 1.13 | 0.18 | 0.15 | 0.18 |

It is seen that the film units of the invention desirably had a significantly smaller $D_{max}$ loss for red and green at 35° C. processing in comparison to 24° C. processing than did the control.

EXAMPLES XXXVI

As a control a film unit was prepared as follows: the negative element comprised an opaque subcoated polyethylene terephthalate film base on which the following layers were coated in succession:

1. as a polymeric acid layer approximately 9 parts of a ½ butyl ester of polyethylene/maleic anhydride copolymer and 1 part of polyvinyl butyral coated at a coverage of about 26.460 mgs/m²;

2. a timing layer coated at a coverage of about 3750 mgs/m² of a 60/29/6/4/0.4 pentapolymer of butylacrylate, diacetone acrylamide, methacrylic acid, styrene and acrylic acid and about 55.8 mgs/m² of gelatin;

3. a cyan dye developer layer comprising about 600 mgs/m² of the cyan dye developer illustrated in Example XXXV, about 300 mgs/m² of gelatin and about 121 mgs/m² of 4'-methylphenylhydroquinone;

4. a layer coated at a coverage of about 1000 mgs/m² of titanium dioxide, about 375 mgs/m² of a polymethylmethacrylate latex, about 125 mgs/m² of gelatin and about 375 mgs/m² of the pentapolymer described in layer 1;

5. a red sensitive silver iodobromide emulsion layer comprising about 1300 mgs/m² of silver and about 780 mgs/m² of gelatin;

6. an interlayer comprising about 3000 mgs/m² of a 60/30/4/6 tetrapolymer of butylacrylate, diacetone acrylamide, styrene and methacrylic acid and about 30 mgs/m² of polyacrylamide;

7. a magenta dye developer layer comprising about 550 mgs/m² of the magenta dye developer illustrated in Example XXXV and about 275 mgs/m² of gelatin;

8. a green sensitive silver iodobromide emulsion layer comprising about 400 mgs/m² of silver and about 176 mgs/m² of gelatin;

9. an interlayer comprising about 2500 mgs/m² of the tetrapolymer described in layer 6, about 30 mgs/m² of polyacrylamide and about 4 mgs/m² of formaldehyde;

10. a layer comprising about 100 mgs/m² of gelatin;

11. a yellow dye developer layer comprising about 775 mgs/m² of the yellow dye developer illustrated in Example XXXV and about 310 mgs/m² of gelatin;

12. a layer comprising about 250 mgs/m² of titanium dioxide, about 187.5 mgs/m² of a polymethylmethacrylate latex and about 31.25 mgs/m² of gelatin;

13. a blue sensitive silver iodobromide emulsion layer coated at a coverage of about 950 mgs/m² of silver and about 475 mgs/m² of gelatin;

14. a layer comprising about 250 mgs/m² of 4'-methyl phenyl hydroquinone and about 110 mgs/m² of gelatin; and 15. a layer comprising about 484 mgs/m² of gelatin.

The image-receiving element comprised a transparent subcoated polyethylene terephthalate film base upon which there was coated an image receiving layer as described in Example XXXV and a topcoat layer comprising about 100 mgs/ft² of unhardened gelatin.

The film unit was processed with a processing composition made up as follows:

| | Weight Percent |
|---|---|
| TiO₂ | 48.0 |
| Oximated polydiacetone acrylamide | 0.66 |
| Potassium hydroxide | 4.37 |
| Benzotriazole | 0.46 |
| 4-aminopyrazolo-(3,4-d)pyrimidine | 0.21 |
| 6-methyluracil | 0.25 |
| N—hydroxyethyl-N,N',N'—triscarboxymethyl ethylene diamine | 0.62 |
| Polyethylene glycol (M.W. 4000) | 0.37 |
| Colloidal silica (30% solids) | 0.77 |
| 6-bromo-5-methyl-4-azabenzimidazole | 0.10 |
| N—phenethyl-α-picolinium bromide | 2.12 |
| Allopurinol | 0.068 |
| 3,5-dimethylpyrazole | 0.17 |
| 2-methylimidazole | 0.69 |

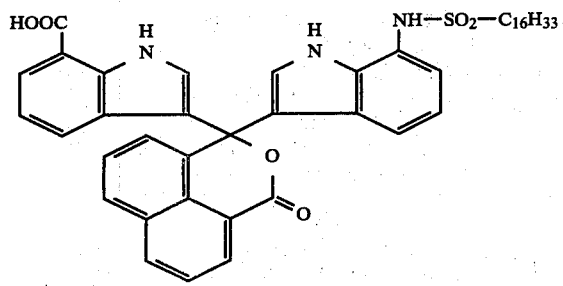

0.3

| | Weight Percent |
|---|---|
| 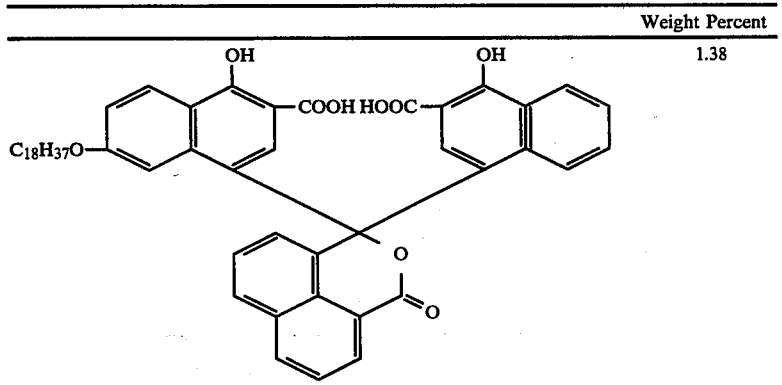 | 1.38 |
| Water to make 100% | |

The film unit was exposed (0.5 meter-candle-second through the transparent base of the image receiving element on a sensitometer to a test exposure scale with white light and processed at room temperature (24° C.) by passing the film unit through a pair of rollers at a gap spacing of about 76 microns. Identical film units were processed in the same manner at 13° C. and 35° C. respectively. The neutral density columns of the images were read on a densitometer to obtain the $D_{max}$ and $D_{min}$ values for red, green and blue respectively. In addition the speeds of the red, green and blue curves respectively (defined as the negative log of the relative exposure required to give red, green and blue absorption, respectively, in the neutral column a reflection density of 0.75) were measured. The values are shown in Table III.

EXAMPLE XXXVII

The experiment described in Example XXXVI was repeated with film units according to the invention. These film units were the same as those described in Example XXXVI with the exception that layers 7 and 15 of the negative element each further included compounds of the invention in the amounts shown below.

| Film Unit | Compound | Amounts (Mgs/m²) |
|---|---|---|
| XXXVII A | IV | 84 0 |
| XXXVII B | XI | 87.6 |
| XXXVII C | XXVI | 98.5 |

The amounts of the compounds were selected so as to provide approximately equal molar amounts of each. These film units were processed at 13° C., 24° C. and 35° C. The results are shown in Table III.

TABLE III

| | | R | G | B | Speed R | G | B |
|---|---|---|---|---|---|---|---|
| | | | 13° C. | | | | |
| Control | Dmax | 1.91 | 2.12 | 1.66 | 2.12 | 2.21 | 2.28 |
| | Dmin | 0.24 | 0.19 | 0.19 | | | |
| XXXVII A | Dmax | 1.96 | 2.25 | 1.74 | 1.80 | 1.78 | 2.01 |
| | Dmin | 0.25 | 0.22 | 0.24 | | | |
| XXXVII B | Dmax | 1.90 | 2.25 | 1.56 | 1.90 | 1.98 | 2.14 |
| | Dmin | 0.26 | 0.22 | 0.23 | | | |
| XXXVII C | Dmax | 1.89 | 2.36 | 1.97 | 1.87 | 1.88 | 2.00 |
| | Dmin | 0.25 | 0.22 | 0.25 | | | |
| | | | 24° C. | | | | |
| Control | Dmax | 2.12 | 1.94 | 1.42 | 2.25 | 2.39 | 2.51 |
| | Dmin | 0.24 | 0.20 | 0.19 | | | |

TABLE III-continued

| | | R | G | B | Speed R | G | B |
|---|---|---|---|---|---|---|---|
| XXXVII A | Dmax | 2.24 | 2.32 | 1.62 | 2.07 | 1.77 | 2.18 |
| | Dmin | 0.24 | 0.20 | 0.22 | | | |
| XXXVII B | Dmax | 2.23 | 2.29 | 1.51 | 2 15 | 2.15 | 2.36 |
| | Dmin | 0.25 | 0.20 | 0.22 | | | |
| XXXVII C | Dmax | 2.20 | 2.36 | 1.84 | 2.13 | 2.06 | 2.22 |
| | Dmin | 0.24 | 0.19 | 0.23 | | | |
| | | | 35° C. | | | | |
| Control | Dmax | 1.53 | 1.30 | 0.96 | 2.35 | 2.53 | 2.71 |
| | Dmin | 0.23 | 0.21 | 0.22 | | | |
| XXXVII A | Dmax | 2.16 | 1.89 | 1.20 | 2.26 | 1.83 | 2.44 |
| | Dmin | 0.25 | 0.22 | 0.25 | | | |
| XXXVII B | Dmax | 2.13 | 1.92 | 1.20 | 2.29 | 2.23 | 2.51 |
| | Dmin | 0.25 | 0.21 | 0.24 | | | |
| XXXVII C | Dmax | 2.17 | 2.14 | 1.54 | 2.29 | 2.11 | 2.36 |
| | Dmin | 0.24 | 0.20 | 0.24 | | | |

It is seen that the film units according to the invention desirably had significantly smaller red, green and blue $D_{max}$ losses at 35° C. processing in comparison to processing at 24° C. than did the control.

EXAMPLE XXXVIII

As a control a film unit was prepared as follows: the negative element was the same as that described in Example XXXVI except that layer 10 further included about 250 mgs/m² of 2-phenylbenzimidazole. The image-receiving element and the processing composition were the same as those described in Example XXXVI.

In addition, film units according to the invention were prepared. These were identical to the control with the with the exception that in one (Film Unit XXXVIII A) the negative further included a topcoat layer comprising about 20 mgs/ft² of compound XI and about 20 mgs/ft² of gelatin and in the other (Film Unit XXXVIII B) the negative further included a topcoat layer comprising about 20 mgs/ft² of compound XXVI and about 20 mgs/ft² of gelatin.

The film units were processed at 13° C., 24° C. and 35° C. respectively by exposing the negative (0.5 meter-candle-second) on a sensitometer to a test exposure scale with white light and then bringing the negative together with the image-receiving element and passing them through a pair of rollers set at a gap of about 0.0026 inch. The film units were kept intact and viewed through the base of the image-receiving element. The results are shown in Table IV.

TABLE IV

|  | Dmax | | | Dmin | | |
|---|---|---|---|---|---|---|
|  | R | G | B | R | G | B |
| 13° C. | | | | | | |
| Control | 1.45 | 1.96 | 2.03 | 0.21 | 0.21 | 0.22 |
| XXXVIII A | 1.40 | 1.85 | 2.02 | 0.21 | 0.21 | 0.25 |
| XXXVIII B | 1.51 | 1.97 | 2.06 | 0.20 | 0.20 | 0.25 |
| 24° C. | | | | | | |
| Control | 1.75 | 2.07 | 2.03 | 0.21 | 0.20 | 0.19 |
| XXXVIII A | 1.71 | 1.98 | 1.87 | 0.21 | 0.19 | 0.22 |
| XXXVIII B | 1.71 | 2.04 | 2.04 | 0.20 | 0.19 | 0.25 |
| 35° C. | | | | | | |
| Control | 1.39 | 1.45 | 1.79 | 0.21 | 0.20 | 0.21 |
| XXXVIII A | 1.77 | 1.61 | 1.64 | 0.20 | 0.20 | 02.4 |
| XXXVIII B | 1.74 | 1.70 | 1.72 | 0.21 | 0.20 | 0.27 |

It is seen that the film units of the invention exhibited significantly superior performance at 35° C. in comparison to 24° C. that did the control.

Although the invention has been described with respect to various specific preferred embodiments it is not intended to be limited thereto but rather those skilled in the art will recognize that variations and modifications may be made therein which are within the spirit of the invention and the scope of the appended claims.

What is claimed is:

1. A compound represented by the formula

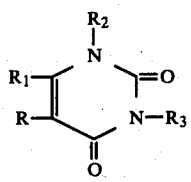

wherein R is

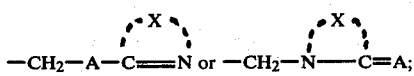

A is sulfur or selenium; X represents the nonmetallic atoms necessary to form a nucleus which completes a tetrazole moiety; $R_1$ is H or alkyl having from 1 to 6 carbon atoms; $R_2$ is H or a group which is hydrolyzable upon contact with an aqueous alkaline medium; and $R_3$ is H, alkyl or a group which is hydrolyzable upon contact with an aqueous alkaline medium.

2. A compound as defined in claim 1 wherein R is

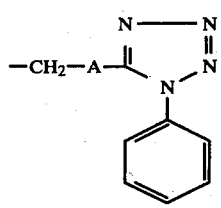

3. A compound as defined in claim 1 wherein R is

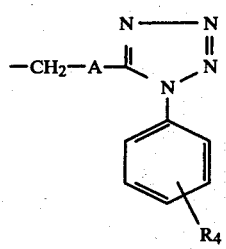

wherein $R_4$ is either a group having a pKa of from about 7 to about 14 which is ionizable to an anion whereby the silver salt of the moiety resulting from the cleavage of R is more soluble in the pH range within which $R_4$ is ionized to an anion than it is below that pH range, or a precursor thereof, said precursor being capable of being converted to $R_4$ upon contact with an aqueous alkaline medium.

4. A compound as defined in claim 3 wherein $R_4$ is selected from the group consisting of

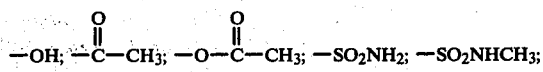

$-SO_2NHC_8H_{17}$; $-NHSO_2CH_3$; $-NHSO_2-$$-CH_3$ and

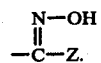

where Z is H, alkyl having from 1 to 10 carbon atoms, benzyl, phenethyl or phenyl.

5. A compound as defined in claim 4 wherein $R_4$ is $-OH$, $-SO_2NH_2$ or

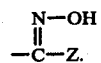

6. A compound as defined in claim 1 wherein $R_2$ and $R_3$ are each H or a hydrolyzable group selected from the group consisting of acetyl, benzoyl, $-CH_2-CH_2-Y$ or an ester group represented by the formula

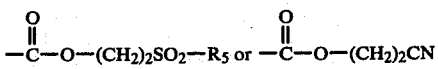

where $R_5$ is alkyl or phenyl and Y is CN,

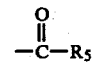

or $-SO_2-R_5$.

7. A compound as defined in claim 1 which is represented by the formula

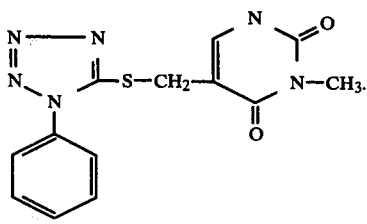

8. A compound as defined in claim 1 which is represented by the formula

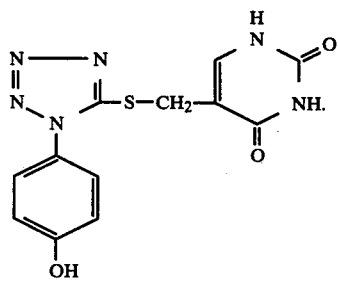

9. A compound as defined in claim 1 which is represented by the formula

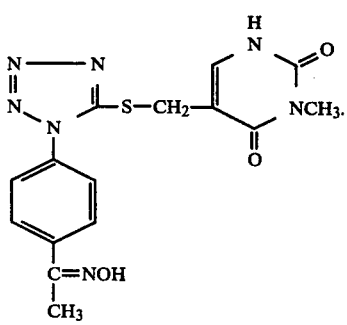

10. A compound represented by the formula

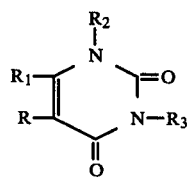

wherein R is

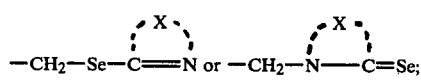

X represents the nonmetallic atoms necessary to form a nucleus which completes a five or six membered heterocyclic moiety; $R_1$ is H or alkyl having from 1 to 6 carbon atoms; $R_2$ is H or a group which is hydrolyzable upon contact with an aqueous alkaline medium; and $R_3$ is H, alkyl or a group which is hydrolyzable upon contact with an aqueous alkaline medium.

11. A compound as defined in claim 10 wherein X represents the nonmetallic atoms which complete a tetrazole moiety.

12. A compound as defined in claim 11 wherein R is

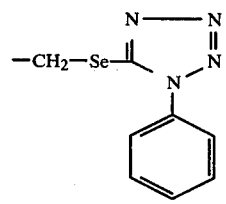

13. A compound as defined in claim 11 wherein R is

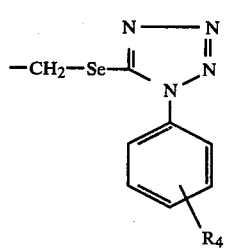

wherein $R_4$ is either a group having pKa of from about 7 to about 14 which is ionizable to an anion whereby the silver salt of the moiety resulting from cleavage of R is more soluble in the pH range within which $R_4$ is ionized to an anion than it is below that pH range, or a precursor thereof, said precursor being capable of being converted to $R_4$ upon contact with an aqueous alkaline medium.

14. A compound as defined in claim 13 wherein $R_4$ is selected from the group consisting of

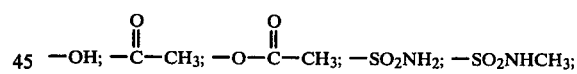

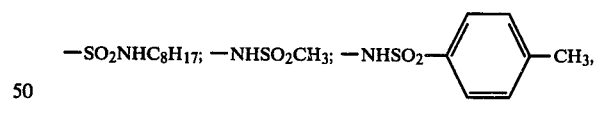

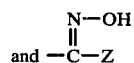

where Z is H, alkyl having from 1 to 10 carbon atoms, benzyl, phenethyl or phenyl.

15. A compound represented by the formula

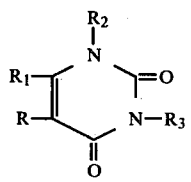

wherein R is

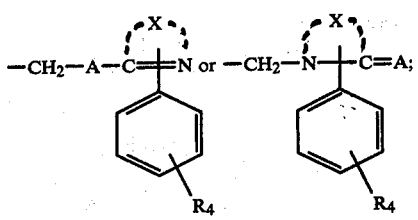

A is sulfur or selenium; X represents the nonmetallic atoms necessary to form a nucleus which completes a five or six membered heterocyclic moiety; $R_1$ is H or alkyl having from 1 to 6 carbon atoms; $R_2$ is H or a group which is hydrolyzable upon contact with an aqueous alkaline medium; $R_3$ is H, alkyl or a group which is hydrolyzable upon contact with an aqueous alkaline medium; and $R_4$ is either a group having a pKa of from about 7 to about 14 which is ionizable to an anion whereby the silver salt of the moiety resulting from cleavage of R is more soluble in the pH range within which $R_4$ is ionized to an anion that it is below that pH range or a precursor thereof, said precursor being capable of being converted to $R_4$ upon contact with an aqueous alkaline medium.

16. A compound as defined in claim 15 wherein $R_4$ is selected from the group consisting of

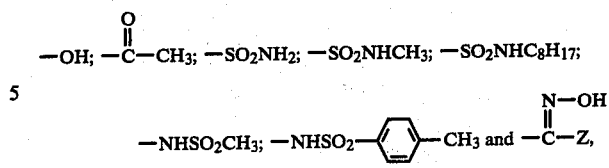

where Z is H, alkyl having from 1 to 10 carbon atoms benzyl, phenethyl or phenyl.

17. A compound as defined in claim 16 wherein $R_4$ is —OH, —SO$_2$NH$_2$

18. A compound as defined in claim 17 wherein $R_2$ and $R_3$ are each H or a hydrolyzable group selected from the group consisting of acetyl, benzoyl, —CH$_2$—CH$_2$—Y or an ester group represented by the formula

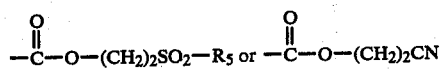

wherein $R_5$ is alkyl or phenyl and Y is CN,

or —SO$_2$R$_5$.

* * * * *